(12) United States Patent
Cooper et al.

(10) Patent No.: US 11,734,231 B2
(45) Date of Patent: Aug. 22, 2023

(54) SYSTEM AND METHODS FOR BANDWIDTH-EFFICIENT ENCODING OF GENOMIC DATA

(71) Applicant: AtomBeam Technologies Inc., Moraga, CA (US)

(72) Inventors: Joshua Cooper, Columbia, SC (US); Aliasghar Riahi, Orinda, CA (US)

(73) Assignee: ATOMBEAM TECHNOLOGIES INC., Moraga, CA (US)

( * ) Notice: Subject to any disclaimer, the term of this patent is extended or adjusted under 35 U.S.C. 154(b) by 0 days.

(21) Appl. No.: 17/569,500

(22) Filed: Jan. 5, 2022

(65) Prior Publication Data

US 2022/0129421 A1  Apr. 28, 2022

Related U.S. Application Data

(63) Continuation-in-part of application No. 16/923,039, filed on Jul. 7, 2020, now Pat. No. 11,232,076, which is a continuation-in-part of application No. 16/716,098, filed on Dec. 16, 2019, now Pat. No. 10,706,018, said application No. 16/716,098 is a continuation of application No. 16/455,655, filed on Jun. 27, 2019, now Pat. No. 10,509,771, which is a continuation-in-part of application No. 16/200,466, filed on Nov. 26, 2018, now Pat. No. 10,476,519, which is a continuation-in-part of application No. 15/975,741, filed on May 9, 2018, now Pat. No. 10,303,391.

(60) Provisional application No. 63/027,166, filed on May 19, 2020, provisional application No. 62/926,723, filed on Oct. 28, 2019, provisional application No. 62/578,824, filed on Oct. 30, 2017.

(51) Int. Cl.
*G06F 16/174* (2019.01)
*G06F 3/06* (2006.01)

(52) U.S. Cl.
CPC ......... *G06F 16/1752* (2019.01); *G06F 3/067* (2013.01); *G06F 3/0608* (2013.01); *G06F 3/0641* (2013.01)

(58) Field of Classification Search
None
See application file for complete search history.

(56) References Cited

U.S. PATENT DOCUMENTS

| | | |
|---|---|---|
| 9,715,574 B2 | 7/2017 | Baym et al. |
| 10,790,044 B2 | 9/2020 | Semenyuk |
| 10,902,937 B2 | 1/2021 | Sheinin et al. |
| 11,093,547 B2 | 8/2021 | Su et al. |

(Continued)

*Primary Examiner* — Michael Alsip
(74) *Attorney, Agent, or Firm* — Galvin Patent Law LLC; Brian R. Galvin

(57) ABSTRACT

A system and methods for bandwidth-efficient encoding of genome and bioinformatic sequence datasets comprising a sequence analyzer configured to: analyze a received sequence dataset to determine a sequence dataset file type, scan the sequence dataset to maintain a count of unique characters contained therein, identify positions where the unique character count increases by a power of two, deconstruct the sequence dataset into a plurality of sourceblocks at the identified positions, and encode the plurality of sourceblocks using a data deconstruction engine and library management module to assign each sourceblock a reference code.

10 Claims, 39 Drawing Sheets

(56) References Cited

U.S. PATENT DOCUMENTS

| | | | | |
|---|---|---|---|---|
| 2012/0222134 A1* | 8/2012 | Orsini | ............... | G06F 21/62 |
| | | | | 726/28 |
| 2013/0282677 A1* | 10/2013 | Ji | ............... | G16B 99/00 |
| | | | | 707/693 |
| 2020/0357483 A1* | 11/2020 | Roquet | ............... | G16B 50/50 |

* cited by examiner

SYSTEM AND METHODS FOR BANDWIDTH-EFFICIENT ENCODING OF GENOMIC DATA

CROSS-REFERENCE TO RELATED APPLICATIONS

Priority is claimed in the application data sheet to the following patents or patent applications, the entire written description of each of which is expressly incorporated herein by reference in its entirety:
Ser. No. 16/923,039
63/027,166
62/926,723
Ser. No. 16/716,098
Ser. No. 16/455,655
Ser. No. 16/200,466
Ser. No. 15/975,741
62/578,824

BACKGROUND OF THE INVENTION

Field of the Invention

The present invention is in the field of computer data storage and transmission, and in particular to the use of block cipher encryption using novel systems and techniques.

Discussion of the State of the Art

As computers become an ever-greater part of our lives, and especially in the past few years, data storage has become a limiting factor worldwide. Prior to about 2010, the growth of data storage far exceeded the growth in storage demand. In fact, it was commonly considered at that time that storage was not an issue, and perhaps never would be, again. In 2010, however, with the growth of social media, cloud data centers, high tech and biotech industries, global digital data storage accelerated exponentially, and demand hit the zettabyte (1 trillion gigabytes) level. Current estimates are that data storage demand will reach 50 zettabytes by 2020. By contrast, digital storage device manufacturers produced roughly 1 zettabyte of physical storage capacity globally in 2016. We are producing data at a much faster rate than we are producing the capacity to store it. In short, we are running out of room to store data, and need a breakthrough in data storage technology to keep up with demand.

The primary solutions available at the moment are the addition of additional physical storage capacity and data compression. As noted above, the addition of physical storage will not solve the problem, as storage demand has already outstripped global manufacturing capacity. Data compression is also not a solution. A rough average compression ratio for mixed data types is 2:1, representing a doubling of storage capacity. However, as the mix of global data storage trends toward multi-media data (audio, video, and images), the space savings yielded by compression either decreases substantially, as is the case with lossless compression which allows for retention of all original data in the set, or results in degradation of data, as is the case with lossy compression which selectively discards data in order to increase compression. Even assuming a doubling of storage capacity, data compression cannot solve the global data storage problem. The method disclosed herein, on the other hand, works the same way with any type of data.

Transmission bandwidth is also increasingly becoming a bottleneck. Large data sets require tremendous bandwidth, and we are transmitting more and more data every year between large data centers. On the small end of the scale, we are adding billions of low bandwidth devices to the global network, and data transmission limitations impose constraints on the development of networked computing applications, such as the "Internet of Things".

Furthermore, as quantum computing becomes more and more imminent, the security of data, both stored data and data streaming from one point to another via networks, becomes a critical concern as existing encryption technologies are placed at risk.

Genomic data science is a field of study that enables researchers to use powerful computational and statistical methods to decode the functional information hidden in DNA sequences. Current estimates predict that genomics research will generate between 2 and 40 exabytes (i.e., $10^{18}$ bytes) of data within the next decade. Data about a single human genome sequence alone would take up 200 gigabytes. Researchers are working to extract valuable information from such complicated and large datasets so they can better understand human health and disease. The scientific community's current ability to sequence DNA has far outpaced its ability to decrypt the information it contains, so genomic data science will be a vibrant field of research for many years to come. Furthermore, performing genomic data science carries with it a set of ethical responsibilities, as each person's sequence data are associated with issues related to privacy and identity. There exists a need for a system and method for bandwidth efficient transmission and storage of compacted genomic data sets.

What is needed is an efficient and secure approach to encryption, storage, and transmission of genomic and bioinformatic datasets.

SUMMARY OF THE INVENTION

The inventor has developed, and reduced to practice, a system and methods for bandwidth-efficient encoding of genome and bioinformatic sequence datasets comprising a sequence analyzer configured to: analyze a received sequence dataset to determine a sequence dataset file type, scan the sequence dataset to maintain a count of unique characters contained therein, identify positions where the unique character count increases by a power of two, deconstruct the sequence dataset into a plurality of sourceblocks at the identified positions, and encode the plurality of sourceblocks using a data deconstruction engine and library management module to assign each sourceblock a reference code.

According to one aspect, a system for bandwidth-efficient encoding of genomic data, comprising: a computing device comprising a processor, a memory, and a first plurality of programming instructions; a codebook stored in the memory of the computing device, the codebook comprising a plurality of sourceblocks and for each sourceblock a reference code; a sequence analyzer comprising a second plurality of programming instructions stored in the memory and operable on the processor, wherein the second plurality of programming instructions, when operating on the processor, cause the processor to: receive a sequence dataset; scan the sequence data and maintain a count of the number of unique characters contained within the sequence data; indicate positions in the sequence where the number of unique characters increase by a power of two; calculate a compaction that would be obtained by dividing the sequence data into one of the plurality of segments at one of the indicated positions that yield the best compaction; deconstruct the sequence dataset into a plurality of sourceblocks at the positions that yield the best compaction; and pass the sourceblocks to a data deconstruction engine; and a data deconstruction engine comprising a third plurality of programming instructions stored in the memory and operable on the processor, wherein the third plurality of programming instructions, when operating on the processor, cause the processor to: receive the sourceblocks from the sequence analyzer; pass the sourceblocks to a library management module for comparison with sourceblocks already contained in the codebook; receive reference codes to the sourceblocks from the library management module and discard the sourceblock; and create a plurality of codewords for storage or transmission of the sequence data; and a library management module comprising a fourth plurality of programming instructions stored in the memory and operable on the processor, wherein the fourth plurality of programming instructions, when operating on the processor, cause the processor to: receive sourceblocks from the data deconstruction engine; return a reference code to the data deconstruction engine, when the sourceblock received matches an existing sourceblock in the codebook; and optimally create new, unique reference codes to the sourceblock received, store both the sourceblock and the associated reference code in the codebook, and return the new reference code to the data deconstruction engine, when that sourceblock does not match an existing sourceblock in the codebook.

In another aspect, a method for bandwidth-efficient encoding of genomic data, comprising the steps of: storing, in a memory of a computing device, a codebook, the codebook comprising a plurality of sourceblocks and for each sourceblock a reference code; receiving a sequence dataset; scanning the sequence data and maintaining a count of the number of unique characters contained within the sequence data; indicating positions in the sequence where the number of unique characters increase by a power of two; calculating a compaction that would be obtained by dividing the sequence data into one of the plurality of segments at one of the indicated positions that yield the best compaction; deconstructing the sequence dataset into a plurality of sourceblocks at the positions that yield the best compaction; passing the sourceblocks to a data deconstruction engine; receiving the sourceblocks from the sequence analyzer; passing the sourceblocks to a library management module for comparison with sourceblocks already contained in the codebook; receiving reference codes to the sourceblocks from the library management module and discard the sourceblock; creating a plurality of codewords for storage or transmission of the sequence data; receiving sourceblocks from the data deconstruction engine; returning a reference code to the data deconstruction engine, when the sourceblock received matches an existing sourceblock in the codebook; and optimally creating new, unique reference codes to the sourceblock received, storing both the sourceblock and the associated reference code in the codebook, and returning the new reference code to the data deconstruction engine, when that sourceblock does not match an existing sourceblock in the codebook.

According to another aspect, each of the plurality of codewords contains at least a reference code to a sourceblock in the codebook, and may contain additional information about the location of the reference code within the sequence dataset.

According to another aspect, the sequence dataset that is encoded comprises a graph representing at least a portion of a plurality of genomes According to another aspect, the graph is a De Bruijin graph, a directed graph, a bi-edged graph, or a bidirected graph.

According to another aspect, the system further comprises a data reconstruction engine comprising a fifth plurality of programming instructions stored in the memory and operable on the processor, wherein the fifth plurality of programming instructions, when operating on the processor, cause the processor to: receive requests for reconstructed sequence data; retrieve the codewords associated with the requested data from the codebook; pass the reference codes contained in the codewords to the library management module for retrieval of the sourceblock contained in the codebook associated with the reference codes; assemble the sourceblock in the proper order based on the location information contained in the codewords; and send out the reconstructed sequence data to the requestor.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

Figure 1:
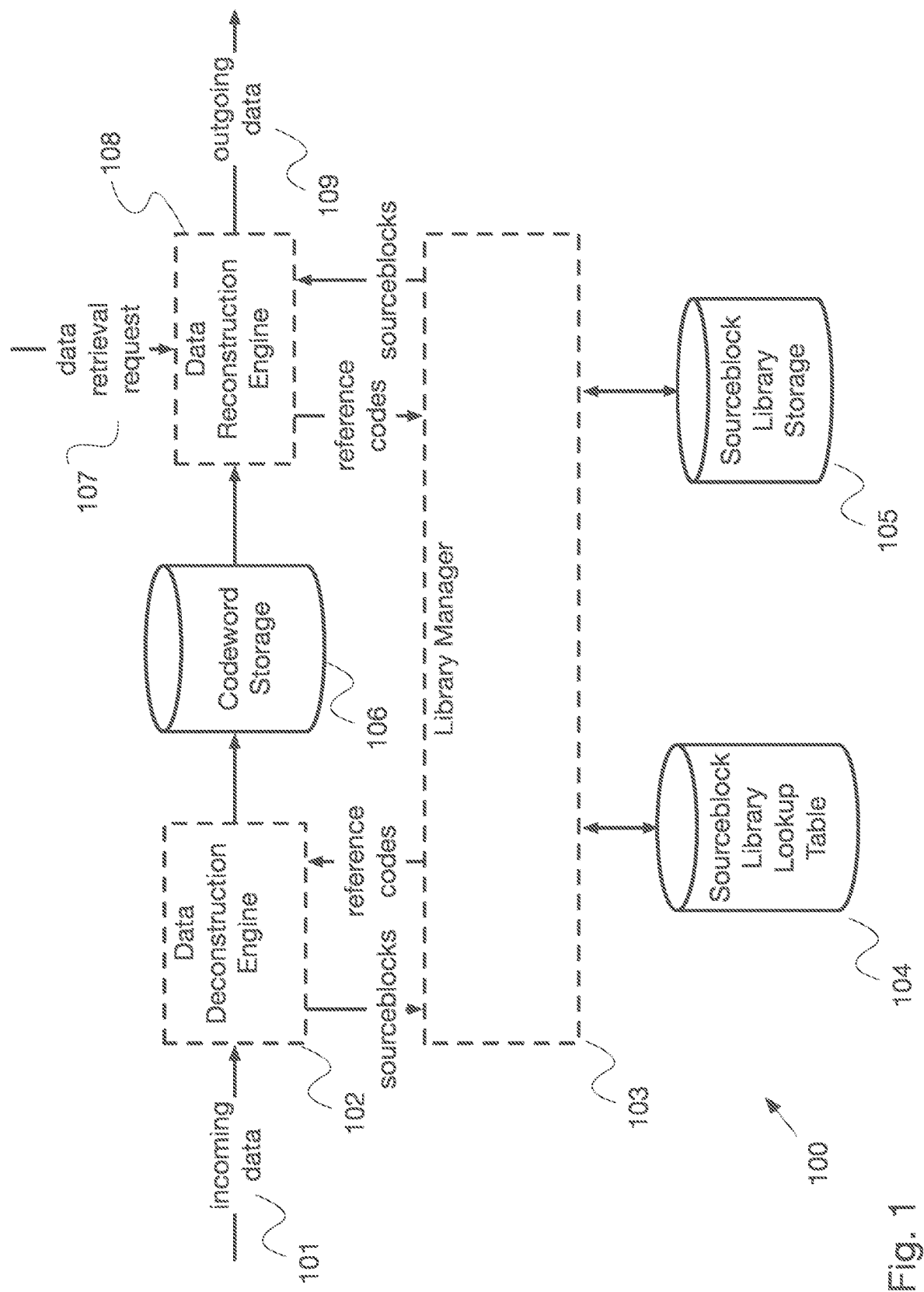
FIG. 1 is a diagram showing an embodiment of the system in which all components of the system are operated locally.

FIGS. 36A-D are exemplary genome graphs that may be processed by a system for bandwidth-efficient encoding of genomic data, according to some embodiments.

DETAILED DESCRIPTION

The inventor has conceived, and reduced to practice, a system and methods for bandwidth-efficient encoding of genome and bioinformatic sequence datasets comprising a sequence analyzer configured to: analyze a received sequence dataset to determine a sequence dataset file type, scan the sequence dataset to maintain a count of unique characters contained therein, identify positions where the unique character count increases by a power of two, deconstruct the sequence dataset into a plurality of sourceblocks at the identified positions, and encode the plurality of sourceblocks using a data deconstruction engine and library management module to assign each sourceblock a reference code.

Genomic data and the analysis thereof is useful because it allows for many breakthroughs in various scientific industries due to the continued research and experimentation regarding genes and genetics, both human and animal alike. Because of the structural nature of genomic data (e.g., its repeatability and length), as well as its scientific value for researchers, it would be beneficial to have a system and method for efficiently transmitting and storing compacted genomic datasets. Such a system and method would allow for scientists and researchers to store and share datasets between and among themselves by greatly reducing the amount of data through one or more data compaction techniques described herein.

Researchers are expected to share human genomic data according to consent provided by the research participants. Genomic data are typically shared with the scientific community through data resources, which can be accessed in three ways. The first way, open-access or unrestricted access is the broadest form of data sharing. Data are available to the public for any research purpose. The next way is with registered access, which falls in between open-access and controlled-access. Researchers can obtain the data for any purpose: however, they must register their information, and their work with the data may be monitored. The final way to access is through controlled-access which requires researchers to describe their research purpose so that a special data access committee can evaluate the consistency of the research purpose with the participant's consent. The researcher can only access the data after receiving the committee's approval. Clearly, there is a need and requirement for genomic data to be kept private with restricted access. The disclosed system and method, their embodiments and various aspects, can provide data compaction, which is inherently made secure during the encoding process, while also providing various other techniques for enhancing the data security aspects described herein.

A common method of storing and visualizing genomic data is with the use of genome graphs. Various types of genome graphs that may be processed and analyzed using the disclosed system and method can include De Bruijin graphs, directed acyclic graphs, bidirected graph (i.e., sequence graph), and biedged graphs (i.e., biedged sequence graphs). Each of these types of genome graphs has pros and cons associated with the structure of the graph and what that type of information is conveyed can depend on the graph structure. Genome graphs include the reference genome together with genetic variation and polymorphic haplotypes. Typically, genome graphs also comprise metadata that describe the sample the DNA/RNA sequence was obtained from. For example, a graph or its nodes may have metadata present that describe the organism, the cell line, and the library-preparation method, among other descriptors. The inclusion of metadata is important because it provides deeper information and allows researchers to make better use of the data.

The disclosed system can provide a specially configured computing device which can capture the structure and data contained within a data sequence set and/or genome graph, encode and compact the sequence data, and store and/or transmit the compacted sequence data in a bandwidth efficient manner that improves upon the state of the art.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

The term "bit" refers to the smallest unit of information that can be stored or transmitted. It is in the form of a binary digit (either 0 or 1). In terms of hardware, the bit is represented as an electrical signal that is either off (representing 0) or on (representing 1).

The term "byte" refers to a series of bits exactly eight bits in length.

The term "codebook" refers to a database containing sourceblocks each with a pattern of bits and reference code unique within that library. The terms "library" and "encoding/decoding library" are synonymous with the term codebook.

The terms "compression" and "deflation" as used herein mean the representation of data in a more compact form than the original dataset. Compression and/or deflation may be either "lossless", in which the data can be reconstructed in its original form without any loss of the original data, or "lossy" in which the data can be reconstructed in its original form, but with some loss of the original data.

The terms "compression factor" and "deflation factor" as used herein mean the net reduction in size of the compressed data relative to the original data (e.g., if the new data is 70% of the size of the original, then the deflation/compression factor is 30% or 0.3.)

The terms "compression ratio" and "deflation ratio", and as used herein all mean the size of the original data relative to the size of the compressed data (e.g., if the new data is 70% of the size of the original, then the deflation/compression ratio is 70% or 0.7.)

The term "data" means information in any computer-readable form.

The term "data set" refers to a grouping of data for a particular purpose. One example of a data set might be a word processing file containing text and formatting information.

The term "effective compression" or "effective compression ratio" refers to the additional amount data that can be stored using the method herein described versus conventional data storage methods. Although the method herein described is not data compression, per se, expressing the additional capacity in terms of compression is a useful comparison.

The term "sourcepacket" as used herein means a packet of data received for encoding or decoding. A sourcepacket may be a portion of a data set.

The term "sourceblock" as used herein means a defined number of bits or bytes used as the block size for encoding or decoding. A sourcepacket may be divisible into a number of sourceblocks. As one non-limiting example, a 1 megabyte sourcepacket of data may be encoded using 512 byte sourceblocks. The number of bits in a sourceblock may be dynamically optimized by the system during operation. In one aspect, a sourceblock may be of the same length as the block size used by a particular file system, typically 512 bytes or 4,096 bytes.

The term "codeword" refers to the reference code form in which data is stored or transmitted in an aspect of the system. A codeword consists of a reference code to a sourceblock in the library plus an indication of that sourceblock's location in a particular data set.

The term "alphabet" refers to the total group of unique characters found within a sequence dataset to be encoded. For example, an exemplary dataset may comprise only the characters of "ABCD", which means the alphabet for this dataset has a size of four because there are four unique characters contained in the dataset, and the dataset's alphabet is described as "A, B, C, D".

Conceptual Architecture

FIG. 1 is a diagram showing an embodiment 100 of the system in which all components of the system are operated locally. As incoming data 101 is received by data deconstruction engine 102. Data deconstruction engine 102 breaks the incoming data into sourceblocks, which are then sent to library manager 103. Using the information contained in sourceblock library lookup table 104 and sourceblock library storage 105, library manager 103 returns reference codes to data deconstruction engine 102 for processing into codewords, which are stored in codeword storage 106. When a data retrieval request 107 is received, data reconstruction engine 108 obtains the codewords associated with the data from codeword storage 106, and sends them to library manager 103. Library manager 103 returns the appropriate sourceblocks to data reconstruction engine 108, which assembles them into the proper order and sends out the data in its original form 109.

Figure 2:
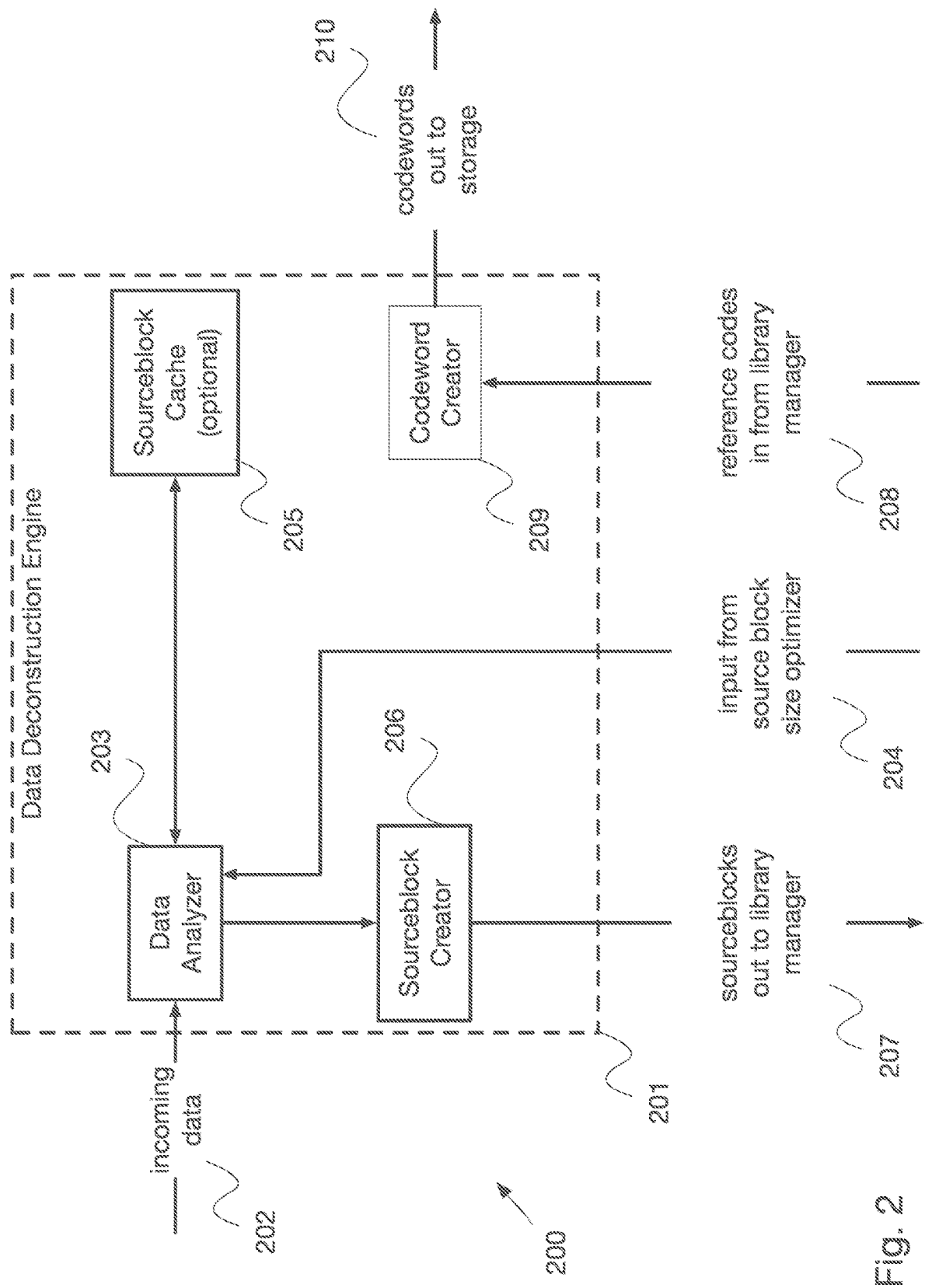
FIG. 2 is a diagram showing an embodiment of one aspect of the system, the data deconstruction engine.

FIG. 2 is a diagram showing an embodiment of one aspect 200 of the system, specifically data deconstruction engine 201. Incoming data 202 is received by data analyzer 203, which optimally analyzes the data based on machine learning algorithms and input 204 from a sourceblock size optimizer, which is disclosed below. Data analyzer may optionally have access to a sourceblock cache 205 of recently-processed sourceblocks, which can increase the speed of the system by avoiding processing in library manager 103. Based on information from data analyzer 203, the data is broken into sourceblocks by sourceblock creator 206, which sends sourceblocks 207 to library manager 203 for additional processing. Data deconstruction engine 201 receives reference codes 208 from library manager 103, corresponding to the sourceblocks in the library that match the sourceblocks sent by sourceblock creator 206, and codeword creator 209 processes the reference codes into codewords comprising a reference code to a sourceblock and a location of that sourceblock within the data set. The original data may be discarded, and the codewords representing the data are sent out to storage 210.

Figure 3:
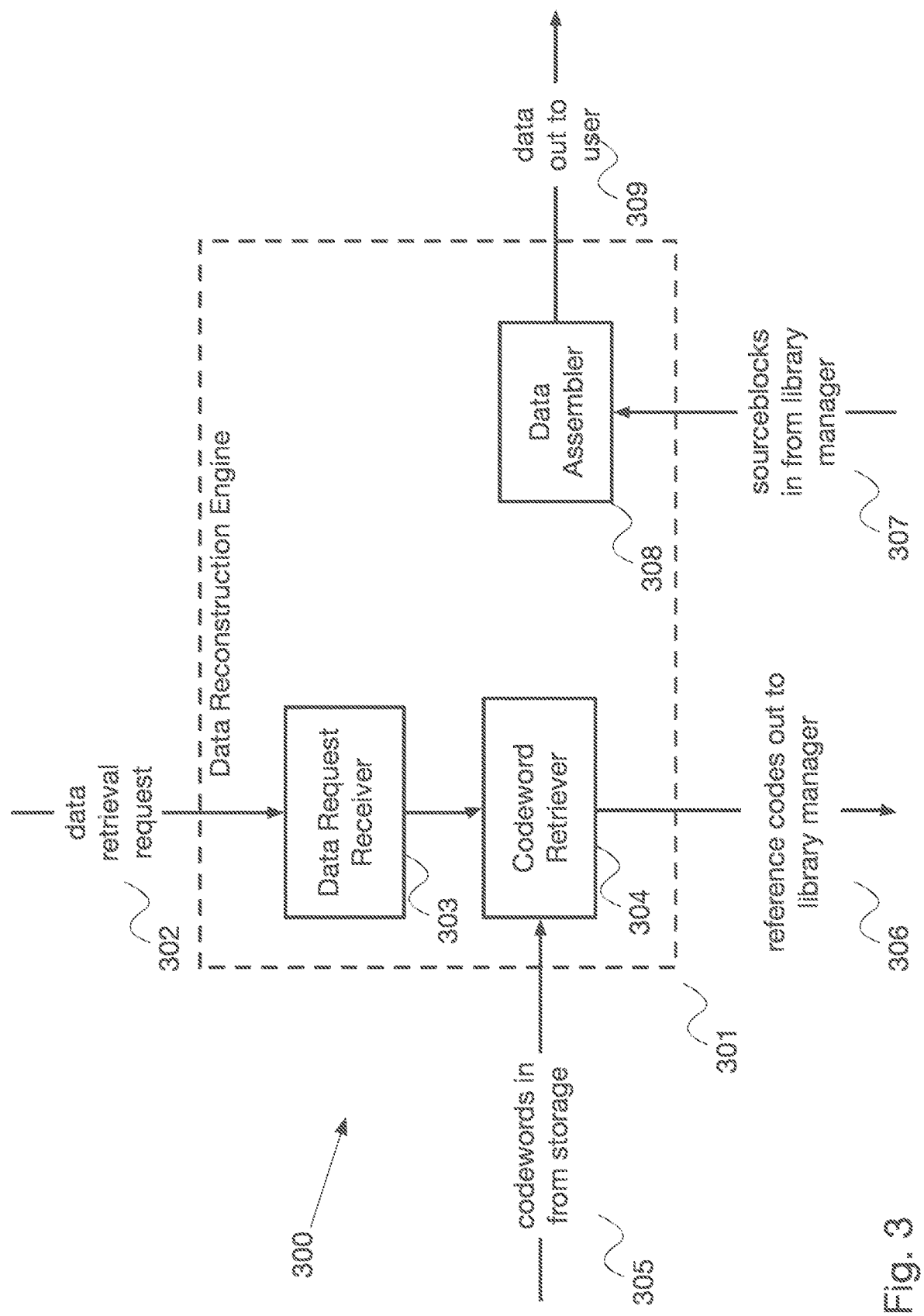
FIG. 3 is a diagram showing an embodiment of one aspect of the system, the data reconstruction engine.

FIG. 3 is a diagram showing an embodiment of another aspect of system 300, specifically data reconstruction engine 301. When a data retrieval request 302 is received by data request receiver 303 (in the form of a plurality of codewords corresponding to a desired final data set), it passes the information to data retriever 304, which obtains the requested data 305 from storage. Data retriever 304 sends, for each codeword received, a reference codes from the codeword 306 to library manager 103 for retrieval of the specific sourceblock associated with the reference code. Data assembler 308 receives the sourceblock 307 from library manager 103 and, after receiving a plurality of sourceblocks corresponding to a plurality of codewords, assembles them into the proper order based on the location information contained in each codeword (recall each codeword comprises a sourceblock reference code and a location identifier that specifies where in the resulting data set the specific sourceblock should be restored to. The requested data is then sent to user 309 in its original form.

Figure 4:
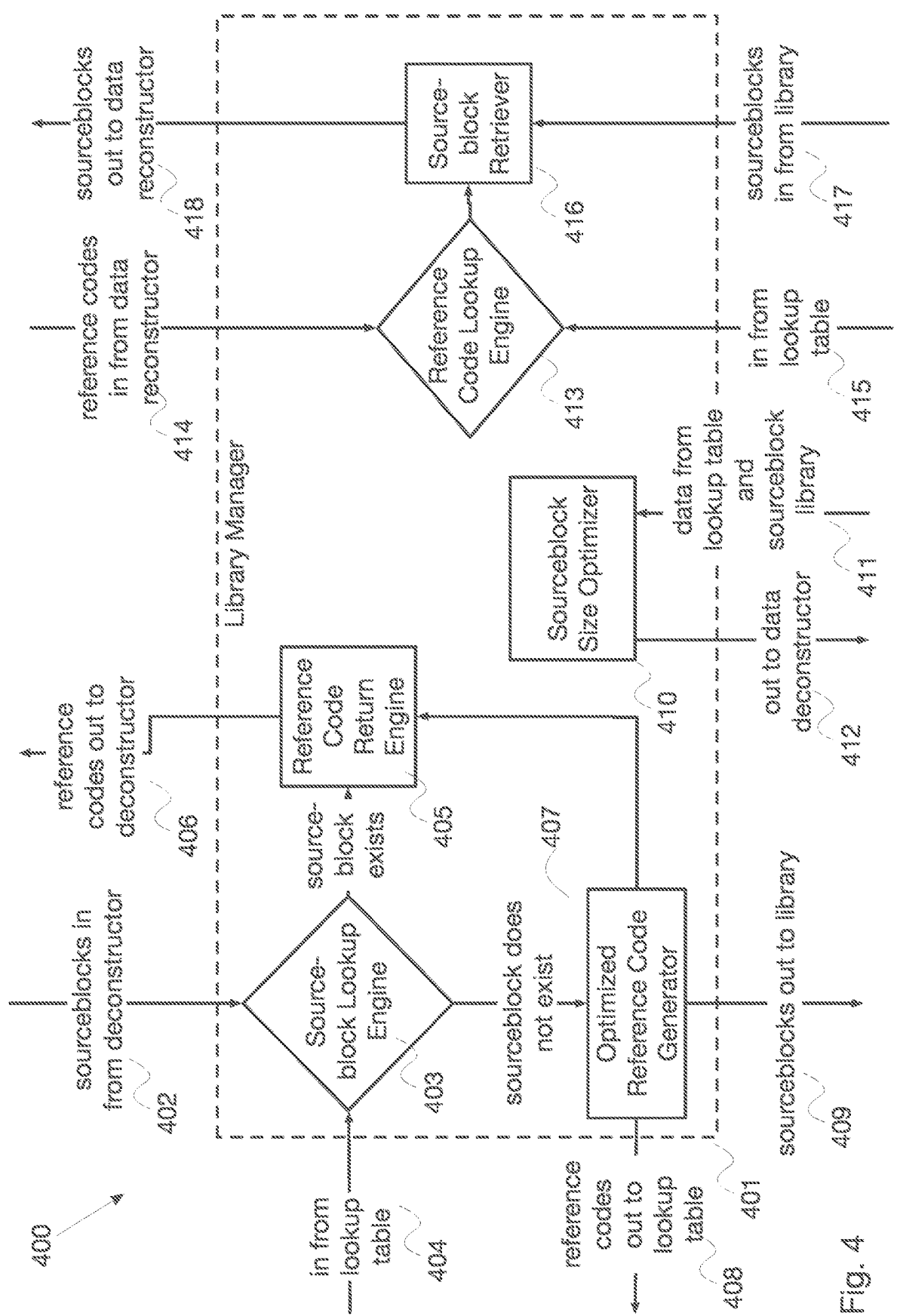
FIG. 4 is a diagram showing an embodiment of one aspect of the system, the library management module.

FIG. 4 is a diagram showing an embodiment of another aspect of the system 400, specifically library manager 401. One function of library manager 401 is to generate reference codes from sourceblocks received from data deconstruction engine 301. As sourceblocks are received 402 from data deconstruction engine 301, sourceblock lookup engine 403 checks sourceblock library lookup table 404 to determine whether those sourceblocks already exist in sourceblock library storage 105. If a particular sourceblock exists in sourceblock library storage 105, reference code return engine 405 sends the appropriate reference code 406 to data deconstruction engine 301. If the sourceblock does not exist in sourceblock library storage 105, optimized reference code generator 407 generates a new, optimized reference code based on machine learning algorithms. Optimized reference code generator 407 then saves the reference code 408 to sourceblock library lookup table 104; saves the associated sourceblock 409 to sourceblock library storage 105; and passes the reference code to reference code return engine 405 for sending 406 to data deconstruction engine 301. Another function of library manager 401 is to optimize the size of sourceblocks in the system. Based on information 411 contained in sourceblock library lookup table 104, sourceblock size optimizer 410 dynamically adjusts the size of sourceblocks in the system based on machine learning algorithms and outputs that information 412 to data analyzer 203. Another function of library manager 401 is to return sourceblocks associated with reference codes received from data reconstruction engine 301. As reference codes are received 414 from data reconstruction engine 301, reference code lookup engine 413 checks sourceblock library lookup table 415 to identify the associated sourceblocks; passes that information to sourceblock retriever 416, which obtains the sourceblocks 417 from sourceblock library storage 105; and passes them 418 to data reconstruction engine 301.

Figure 5:
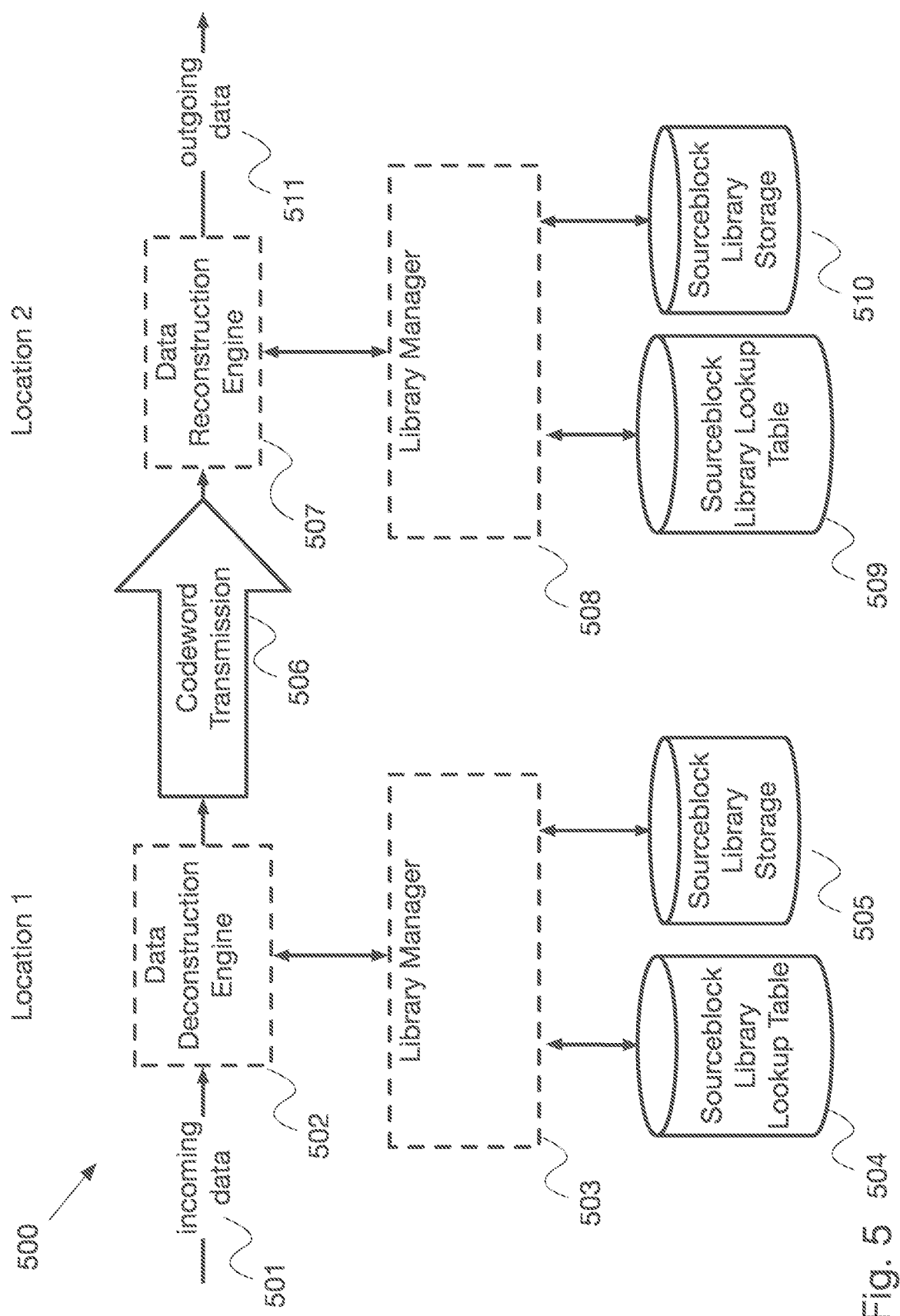
FIG. 5 is a diagram showing another embodiment of the system in which data is transferred between remote locations.

FIG. 5 is a diagram showing another embodiment of system 500, in which data is transferred between remote locations. As incoming data 501 is received by data deconstruction engine 502 at Location 1, data deconstruction engine 301 breaks the incoming data into sourceblocks, which are then sent to library manager 503 at Location 1. Using the information contained in sourceblock library lookup table 504 at Location 1 and sourceblock library storage 505 at Location 1, library manager 503 returns reference codes to data deconstruction engine 301 for processing into codewords, which are transmitted 506 to data reconstruction engine 507 at Location 2. In the case where the reference codes contained in a particular codeword have been newly generated by library manager 503 at Location 1, the codeword is transmitted along with a copy of the associated sourceblock. As data reconstruction engine 507 at Location 2 receives the codewords, it passes them to library manager module 508 at Location 2, which looks up the sourceblock in sourceblock library lookup table 509 at Location 2, and retrieves the associated from sourceblock library storage 510. Where a sourceblock has been transmitted along with a codeword, the sourceblock is stored in sourceblock library storage 510 and sourceblock library lookup table 504 is updated. Library manager 503 returns the appropriate sourceblocks to data reconstruction engine 507, which assembles them into the proper order and sends the data in its original form 511.

Figure 6:
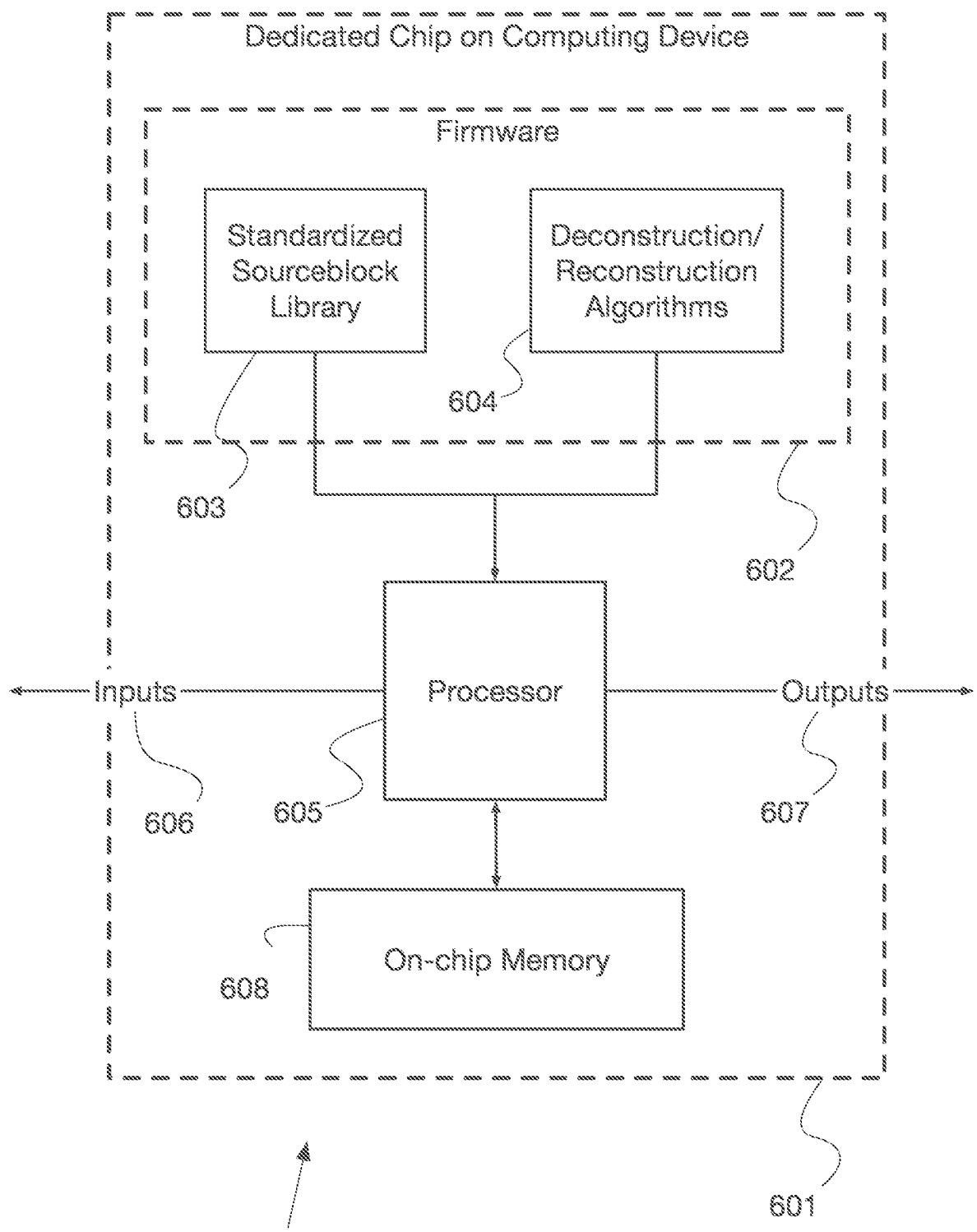
FIG. 6 is a diagram showing an embodiment in which a standardized version of the sourceblock library and associated algorithms would be encoded as firmware on a dedicated processing chip included as part of the hardware of a plurality of devices.

FIG. 6 is a diagram showing an embodiment 600 in which a standardized version of a sourceblock library 603 and associated algorithms 604 would be encoded as firmware 602 on a dedicated processing chip 601 included as part of the hardware of a plurality of devices 600. Contained on dedicated chip 601 would be a firmware area 602, on which would be stored a copy of a standardized sourceblock library 603 and deconstruction/reconstruction algorithms 604 for processing the data. Processor 605 would have both inputs 606 and outputs 607 to other hardware on the device 600. Processor 605 would store incoming data for processing on on-chip memory 608, process the data using standardized sourceblock library 603 and deconstruction/reconstruction algorithms 604, and send the processed data to other hardware on device 600. Using this embodiment, the encoding and decoding of data would be handled by dedicated chip 601, keeping the burden of data processing off device's 600 primary processors. Any device equipped with this embodiment would be able to store and transmit data in a highly optimized, bandwidth-efficient format with any other device equipped with this embodiment.

Figure 12:
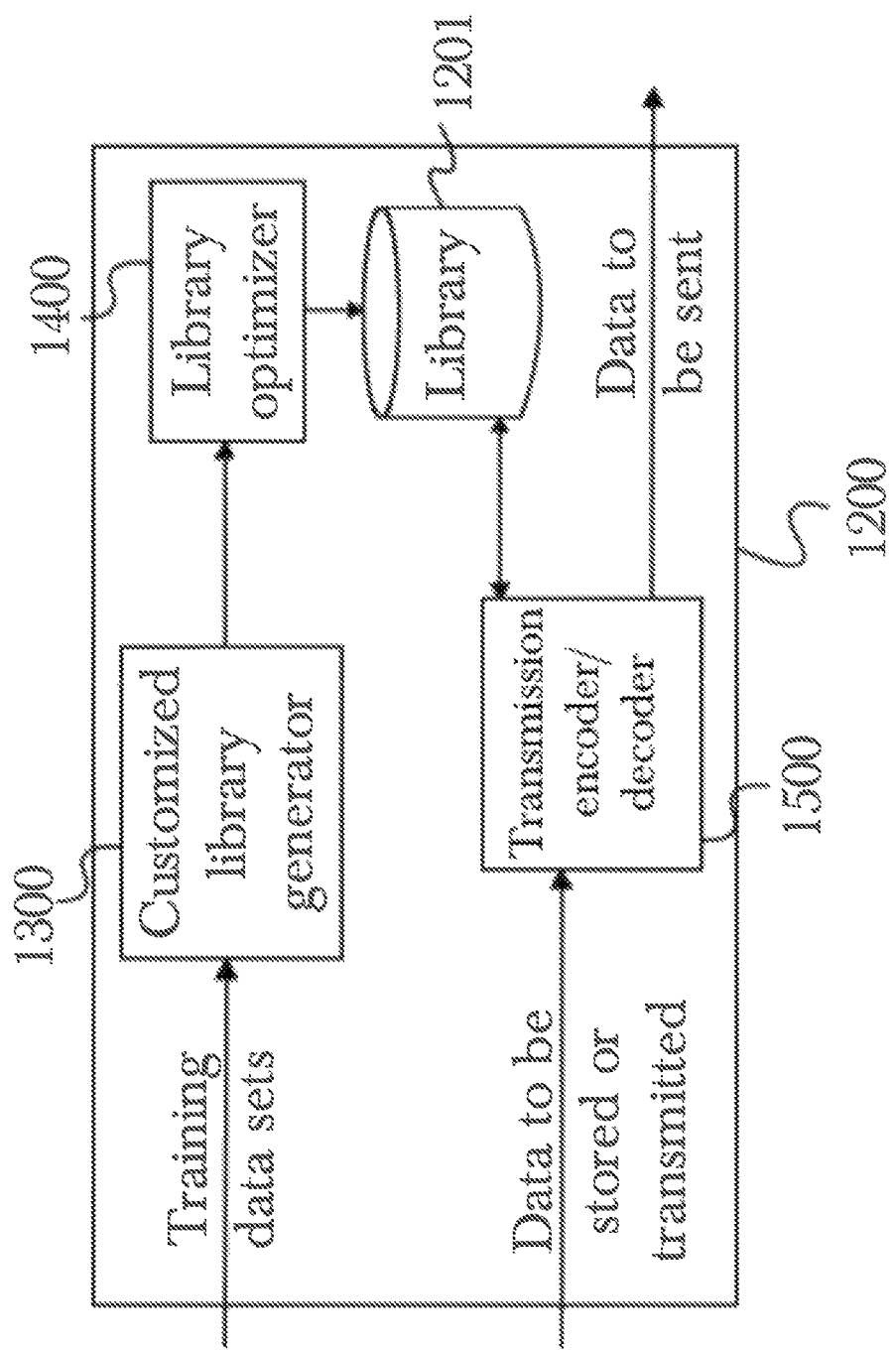
FIG. 12 is a diagram showing an exemplary system architecture, according to a preferred embodiment of the invention.

FIG. 12 is a diagram showing an exemplary system architecture 1200, according to a preferred embodiment of the invention. Incoming training data sets may be received at a customized library generator 1300 that processes training data to produce a customized word library 1201 comprising key-value pairs of data words (each comprising a string of bits) and their corresponding calculated binary Huffman codewords. The resultant word library 1201 may then be processed by a library optimizer 1400 to reduce size and improve efficiency, for example by pruning low-occurrence data entries or calculating approximate codewords that may be used to match more than one data word. A transmission encoder/decoder 1500 may be used to receive incoming data intended for storage or transmission, process the data using a word library 1201 to retrieve codewords for the words in the incoming data, and then append the codewords (rather than the original data) to an outbound data stream. Each of these components is described in greater detail below, illustrating the particulars of their respective processing and other functions, referring to FIGS. 2-4.

System 1200 provides near-instantaneous source coding that is dictionary-based and learned in advance from sample training data, so that encoding and decoding may happen concurrently with data transmission. This results in computational latency that is near zero but the data size reduction is comparable to classical compression. For example, if N bits are to be transmitted from sender to receiver, the compression ratio of classical compression is C the ratio between the deflation factor of system 1200 and that of multi-pass source coding is p, the classical compression encoding rate is $R_C$ bits and the decoding rate is $R_D$ bit/s, and the transmission speed is S bit/s, the compress-send-decompress time will be $$T_{old} = \frac{N}{R_C} + \frac{N}{CS} + \frac{N}{CR_D}$$

while the transmit-while-coding time for system 1200 will be (assuming that encoding and decoding happen at least as quickly as network latency):

$$T_{new} = \frac{N_p}{CS}$$

so that the total data transit time improvement factor is $$\frac{T_{old}}{T_{new}} = \frac{\frac{CS}{R_C} + 1 + \frac{S}{R_D}}{p}$$

which presents a savings whenever $$\frac{CS}{R_C} + \frac{S}{R_D} > p - 1.$$

This is a reasonable scenario given that typical values in real-world practice are C=0.32, $R_C$=1.1·10$^{12}$, $R_D$=4.2·10$^{12}$, S=10$^{11}$, giving $$\frac{CS}{R_C} + \frac{S}{R_D} = 0.053 \ldots,$$

such that system 1200 will outperform the total transit time of the best compression technology available as long as its deflation factor is no more than 5% worse than compression. Such customized dictionary-based encoding will also sometimes exceed the deflation ratio of classical compression, particularly when network speeds increase beyond 100 Gb/s.

The delay between data creation and its readiness for use at a receiving end will be equal to only the source word length t (typically 5-15 bytes), divided by the deflation factor C/p and the network speed S, i.e.

$$delay_{invention} = \frac{tp}{CS}$$

since encoding and decoding occur concurrently with data transmission. On the other hand, the latency associated with classical compression is $$delay_{priorart} = \frac{N}{R_C} + \frac{N}{CS} + \frac{N}{CR_D}$$

where N is the packet/file size. Even with the generous values chosen above as well as N=512K, t=10, and p=1.05, this results in $delay_{invention}$≈3.3·10$^{-10}$ while $delay_{priorart}$≈1.3·10$^{-7}$, a more than 400-fold reduction in latency.

A key factor in the efficiency of Huffman coding used by system 1200 is that key-value pairs be chosen carefully to minimize expected coding length, so that the average deflation/compression ratio is minimized. It is possible to achieve the best possible expected code length among all instantaneous codes using Huffman codes if one has access to the exact probability distribution of source words of a given desired length from the random variable generating them. In practice this is impossible, as data is received in a wide variety of formats and the random processes underlying the source data are a mixture of human input, unpredictable (though in principle, deterministic) physical events, and noise. System 1200 addresses this by restriction of data types and density estimation; training data is provided that is representative of the type of data anticipated in "real-world" use of system 1200, which is then used to model the distribution of binary strings in the data in order to build a Huffman code word library 1200.

Figure 13:
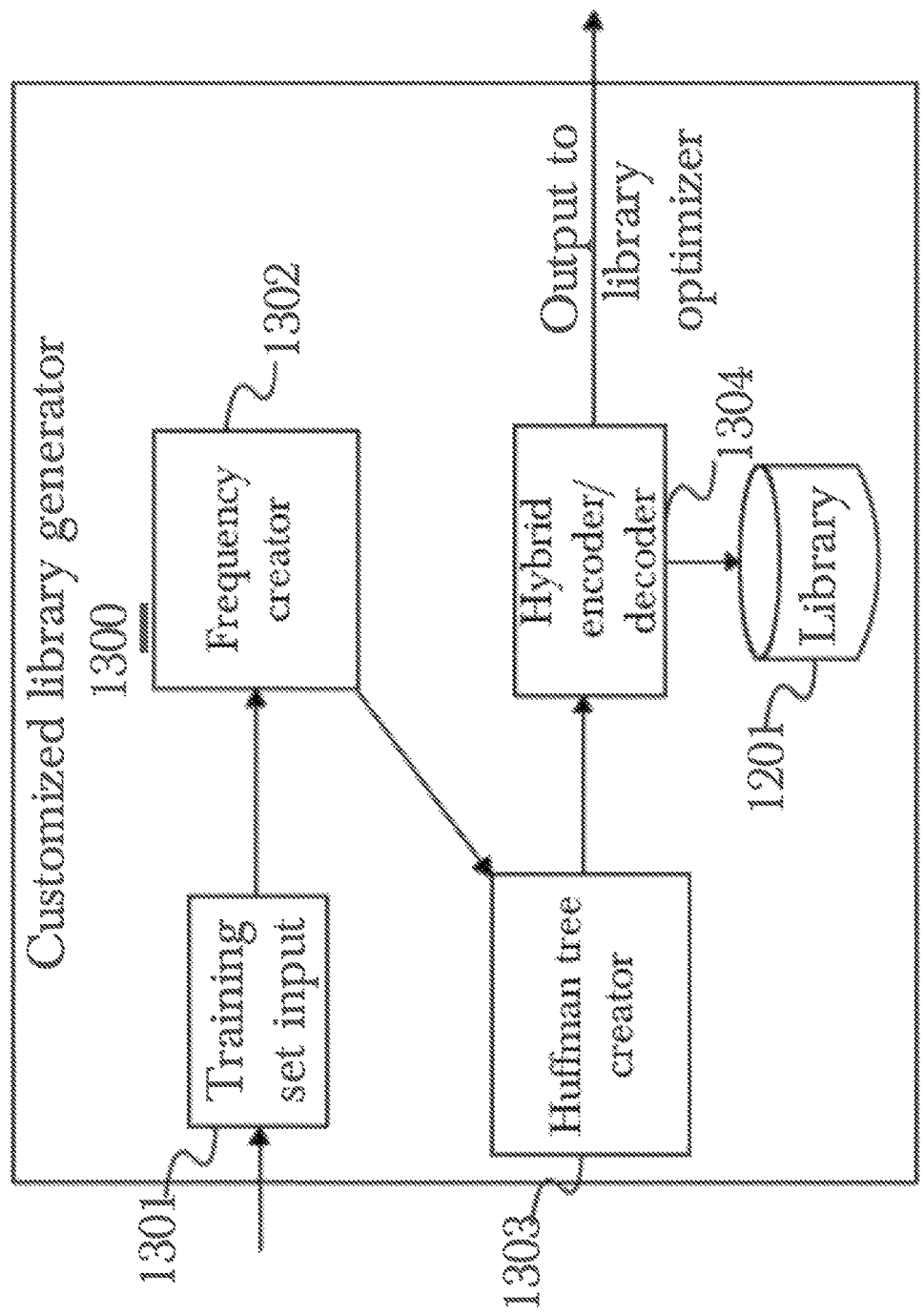
FIG. 13 is a diagram showing a more detailed architecture for a customized library generator.

FIG. 13 is a diagram showing a more detailed architecture for a customized library generator 1300. When an incoming training data set 1301 is received, it may be analyzed using a frequency creator 1302 to analyze for word frequency (that is, the frequency with which a given word occurs in the training data set). Word frequency may be analyzed by scanning all substrings of bits and directly calculating the frequency of each substring by iterating over the data set to produce an occurrence frequency, which may then be used to estimate the rate of word occurrence in non-training data. A first Huffman binary tree is created based on the frequency of occurrences of each word in the first dataset, and a Huffman codeword is assigned to each observed word in the first dataset according to the first Huffman binary tree. Machine learning may be utilized to improve results by processing a number of training data sets and using the results of each training set to refine the frequency estimations for non-training data, so that the estimation yield better results when used with real-world data (rather than, for example, being only based on a single training data set that may not be very similar to a received non-training data set). A second Huffman tree creator 1303 may be utilized to identify words that do not match any existing entries in a word library 1201 and pass them to a hybrid encoder/decoder 1304, that then calculates a binary Huffman codeword for the mismatched word and adds the codeword and original data to the word library 1201 as a new key-value pair. In this manner, customized library generator 1300 may be used both to establish an initial word library 1201 from a first training set, as well as expand the word library 1201 using additional training data to improve operation.

Figure 14:
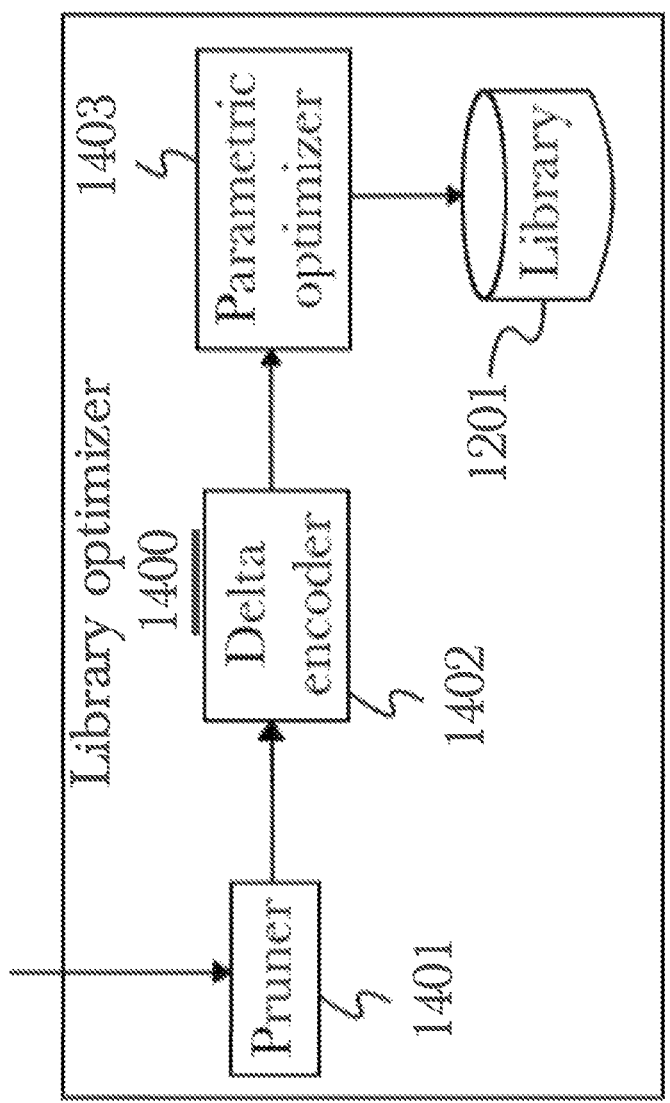
FIG. 14 is a diagram showing a more detailed architecture for a library optimizer.

FIG. 14 is a diagram showing a more detailed architecture for a library optimizer 1400. A pruner 1401 may be used to load a word library 1201 and reduce its size for efficient operation, for example by sorting the word library 1201 based on the known occurrence probability of each key-value pair and removing low-probability key-value pairs based on a loaded threshold parameter. This prunes low-value data from the word library to trim the size, eliminating large quantities of very-low-frequency key-value pairs such as single-occurrence words that are unlikely to be encountered again in a data set. Pruning eliminates the least-probable entries from word library 1201 up to a given threshold, which will have a negligible impact on the deflation factor since the removed entries are only the least-common ones, while the impact on word library size will be larger because samples drawn from asymptotically normal distributions (such as the log-probabilities of words generated by a probabilistic finite state machine, a model well-suited to a wide variety of real-world data) which occur in tails of the distribution are disproportionately large in counting measure. A delta encoder 1402 may be utilized to apply delta encoding to a plurality of words to store an approximate codeword as a value in the word library, for which each of the plurality of source words is a valid corresponding key. This may be used to reduce library size by replacing numerous key-value pairs with a single entry for the approximate codeword and then represent actual codewords using the approximate codeword plus a delta value representing the difference between the approximate codeword and the actual codeword. Approximate coding is optimized for low-weight sources such as Golomb coding, run-length coding, and similar techniques. The approximate source words may be chosen by locality-sensitive hashing, so as to approximate Hamming distance without incurring the intractability of nearest-neighbor-search in Hamming space. A parametric optimizer 1403 may load configuration parameters for operation to optimize the use of the word library 1201 during operation. Best-practice parameter/hyperparameter optimization strategies such as stochastic gradient descent, quasi-random grid search, and evolutionary search may be used to make optimal choices for all interdependent settings playing a role in the functionality of system 1200. In cases where lossless compression is not required, the delta value may be discarded at the expense of introducing some limited errors into any decoded (reconstructed) data.

Figure 15:
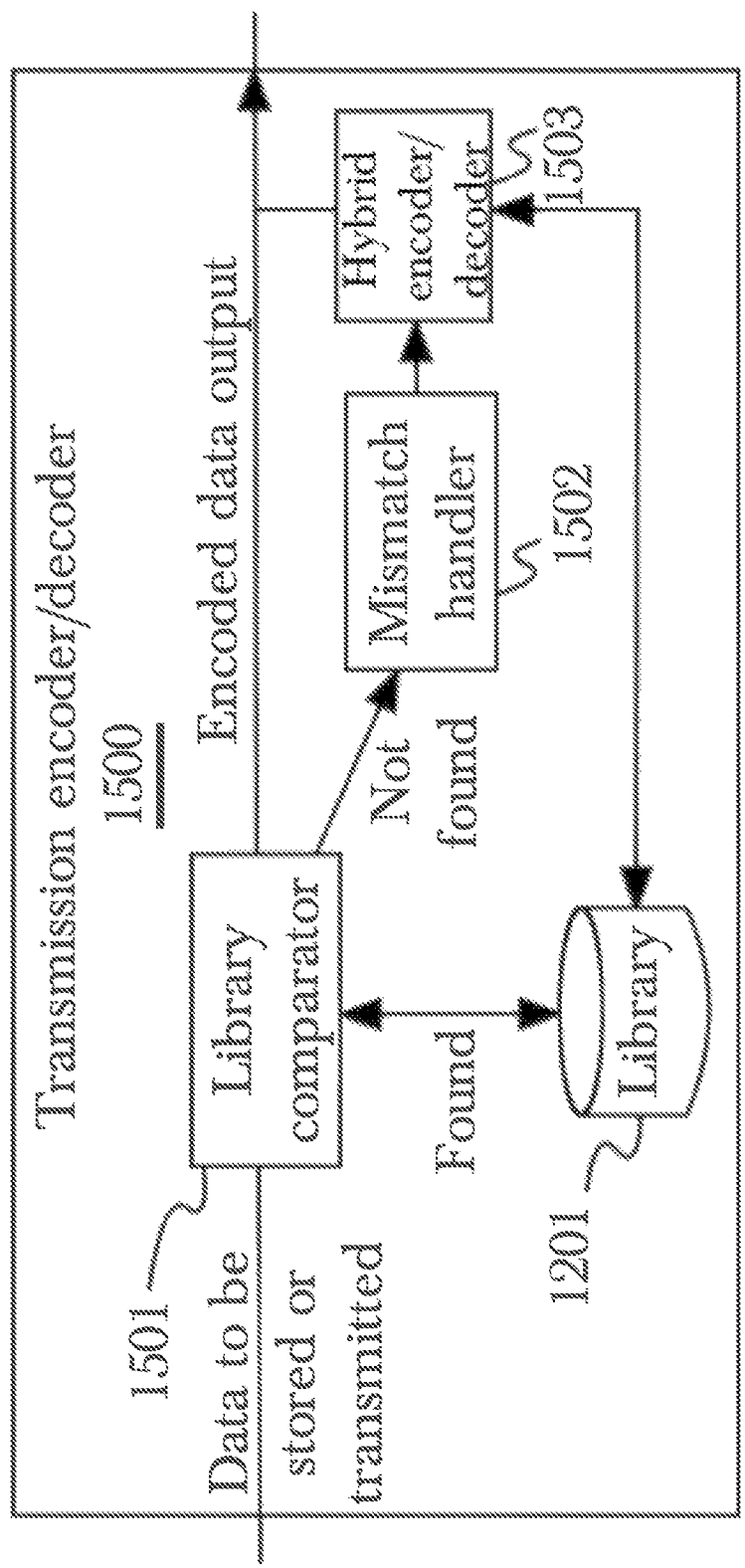
FIG. 15 is a diagram showing a more detailed architecture for a transmission and storage engine.

FIG. 15 is a diagram showing a more detailed architecture for a transmission encoder/decoder 1500. According to various arrangements, transmission encoder/decoder 1500 may be used to deconstruct data for storage or transmission, or to reconstruct data that has been received, using a word library 1201. A library comparator 1501 may be used to receive data comprising words or codewords, and compare against a word library 1201 by dividing the incoming stream into substrings of length t and using a fast hash to check word library 1201 for each substring. If a substring is found in word library 1201, the corresponding key/value (that is, the corresponding source word or codeword, according to whether the substring used in comparison was itself a word or codeword) is returned and appended to an output stream. If a given substring is not found in word library 1201, a mismatch handler 1502 and hybrid encoder/decoder 1503 may be used to handle the mismatch similarly to operation during the construction or expansion of word library 1201. A mismatch handler 1502 may be utilized to identify words that do not match any existing entries in a word library 1201 and pass them to a hybrid encoder/decoder 1503, that then calculates a binary Huffman codeword for the mismatched word and adds the codeword and original data to the word library 1201 as a new key-value pair. The newly-produced codeword may then be appended to the output stream. In arrangements where a mismatch indicator is included in a received data stream, this may be used to preemptively identify a substring that is not in word library 1201 (for example, if it was identified as a mismatch on the transmission end), and handled accordingly without the need for a library lookup.

Figure 19:
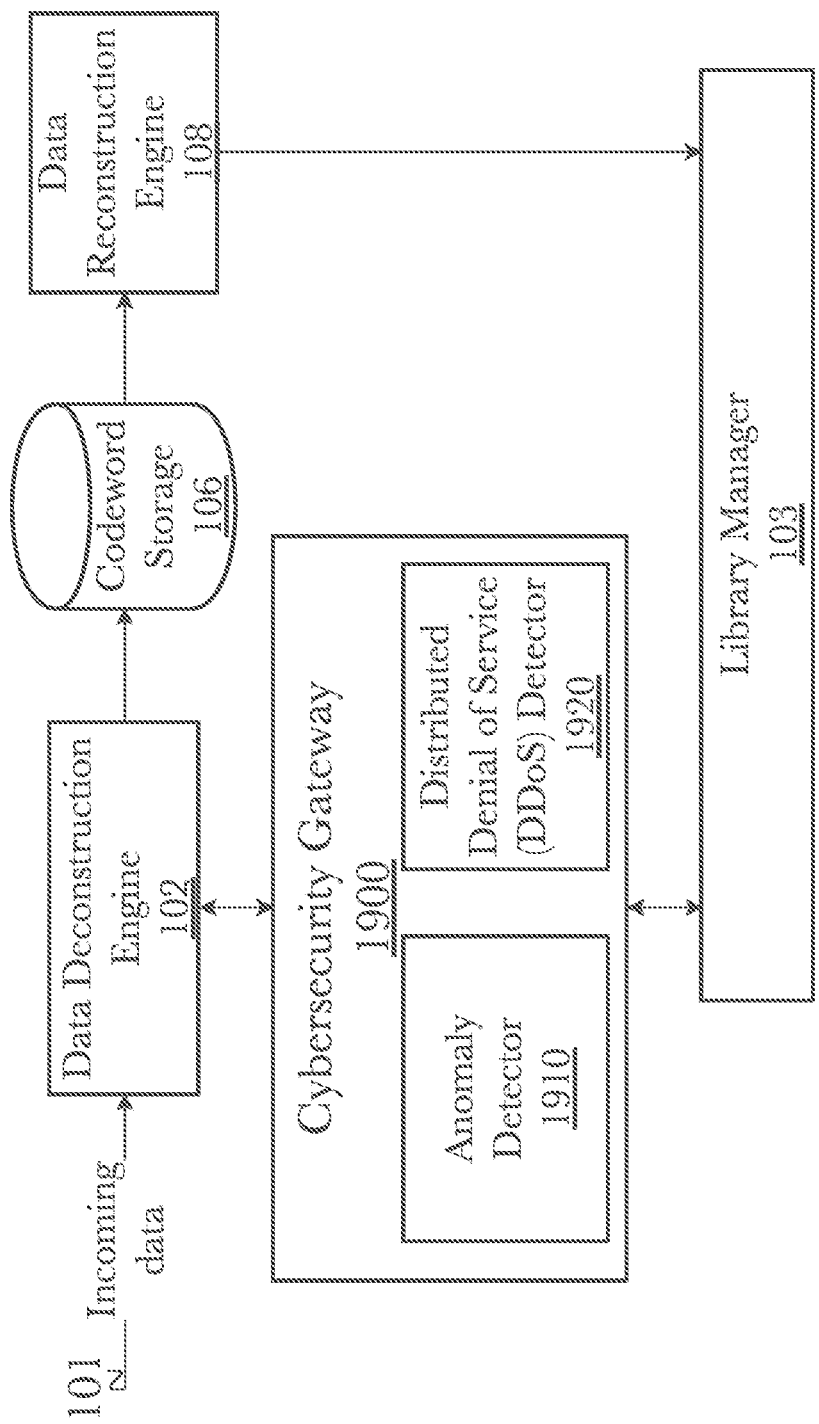
FIG. 19 is an exemplary system architecture of a data encoding system used for cyber security purposes.

FIG. 19 is an exemplary system architecture of a data encoding system used for cyber security purposes. Much like in FIG. 1, incoming data 101 to be deconstructed is sent to a data deconstruction engine 102, which may attempt to deconstruct the data and turn it into a collection of codewords using a library manager 103. Codeword storage 106 serves to store unique codewords from this process, and may be queried by a data reconstruction engine 108 which may reconstruct the original data from the codewords, using a library manager 103. However, a cybersecurity gateway 1900 is present, communicating in-between a library manager 103 and a deconstruction engine 102, and containing an anomaly detector 1910 and distributed denial of service (DDoS) detector 1920. The anomaly detector examines incoming data to determine whether there is a disproportionate number of incoming reference codes that do not match reference codes in the existing library. A disproportionate number of non-matching reference codes may indicate that data is being received from an unknown source, of an unknown type, or contains unexpected (possibly malicious) data. If the disproportionate number of non-matching reference codes exceeds an established threshold or persists for a certain length of time, the anomaly detector 1910 raises a warning to a system administrator. Likewise, the DDoS detector 1920 examines incoming data to determine whether there is a disproportionate amount of repetitive data. A disproportionate amount of repetitive data may indicate that a DDoS attack is in progress. If the disproportionate amount of repetitive data exceeds an established threshold or persists for a certain length of time, the DDoS detector 1910 raises a warning to a system administrator. In this way, a data encoding system may detect and warn users of, or help mitigate, common cyber-attacks that result from a flow of unexpected and potentially harmful data, or attacks that result from a flow of too much irrelevant data meant to slow down a network or system, as in the case of a DDoS attack.

Figure 22:
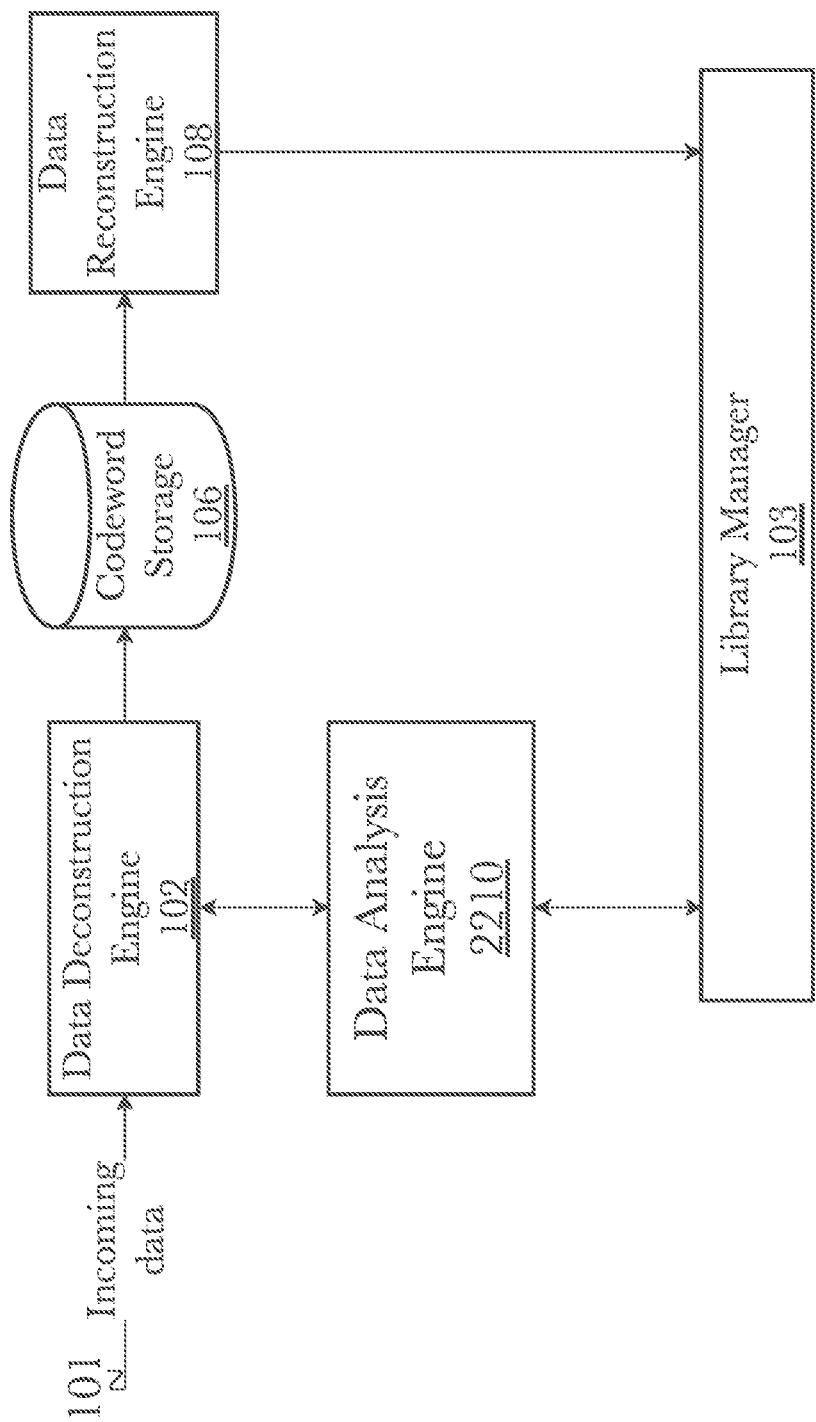
FIG. 22 is an exemplary system architecture of a data encoding system used for data mining and analysis purposes.

FIG. 22 is an exemplary system architecture of a data encoding system used for data mining and analysis purposes. Much like in FIG. 1, incoming data 101 to be deconstructed is sent to a data deconstruction engine 102, which may attempt to deconstruct the data and turn it into a collection of codewords using a library manager 103. Codeword storage 106 serves to store unique codewords from this process, and may be queried by a data reconstruction engine 108 which may reconstruct the original data from the codewords, using a library manager 103. A data analysis engine 2210, typically operating while the system is otherwise idle, sends requests for data to the data reconstruction engine 108, which retrieves the codewords representing the requested data from codeword storage 106, reconstructs them into the data represented by the codewords, and send the reconstructed data to the data analysis engine 2210 for analysis and extraction of useful data (i.e., data mining). Because the speed of reconstruction is significantly faster than decompression using traditional compression technologies (i.e., significantly less decompression latency), this approach makes data mining feasible. Very often, data stored using traditional compression is not mined precisely because decompression lag makes it unfeasible, especially during shorter periods of system idleness. Increasing the speed of data reconstruction broadens the circumstances under which data mining of stored data is feasible.

Figure 24:
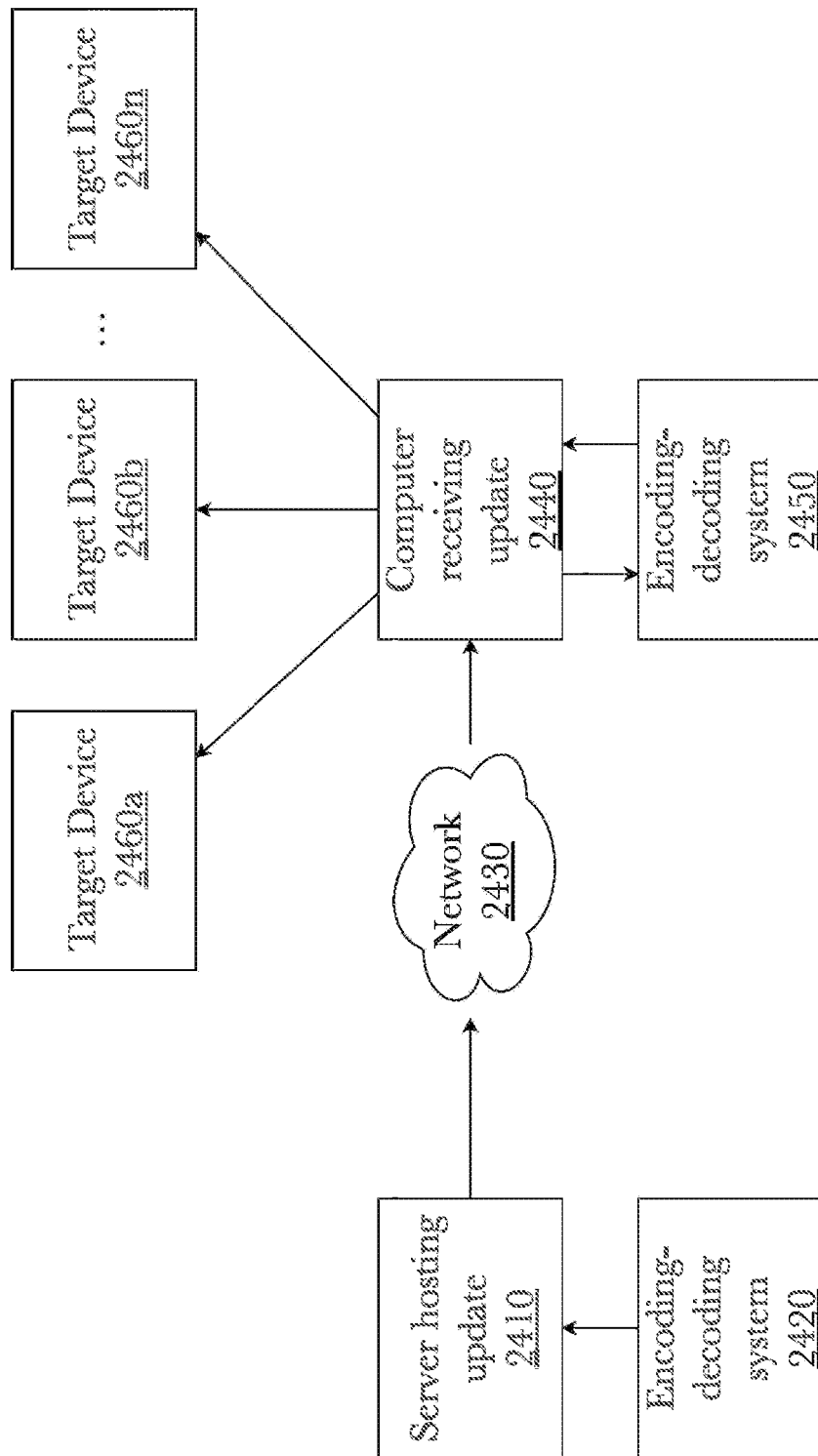
FIG. 24 is an exemplary system architecture of a data encoding system used for remote software and firmware updates.

FIG. 24 is an exemplary system architecture of a data encoding system used for remote software and firmware updates. Software and firmware updates typically require smaller, but more frequent, file transfers. A server which hosts a software or firmware update 2410 may host an encoding-decoding system 2420, allowing for data to be encoded into, and decoded from, sourceblocks or codewords, as disclosed in previous figures. Such a server may possess a software update, operating system update, firmware update, device driver update, or any other form of software update, which in some cases may be minor changes to a file, but nevertheless necessitate sending the new, completed file to the recipient. Such a server is connected over a network 2430, which is further connected to a recipient computer 2440, which may be connected to a server 2410 for receiving such an update to its system. In this instance, the recipient device 2440 also hosts the encoding and decoding system 2450, along with a codebook or library of reference codes that the hosting server 2410 also shares. The updates are retrieved from storage at the hosting server 2410 in the form of codewords, transferred over the network 2430 in the form of codewords, and reconstructed on the receiving computer 2440. In this way, a far smaller file size, and smaller total update size, may be sent over a network. The receiving computer 2440 may then install the updates on any number of target computing devices 2460a-n, using a local network or other high-bandwidth connection.

Figure 26:
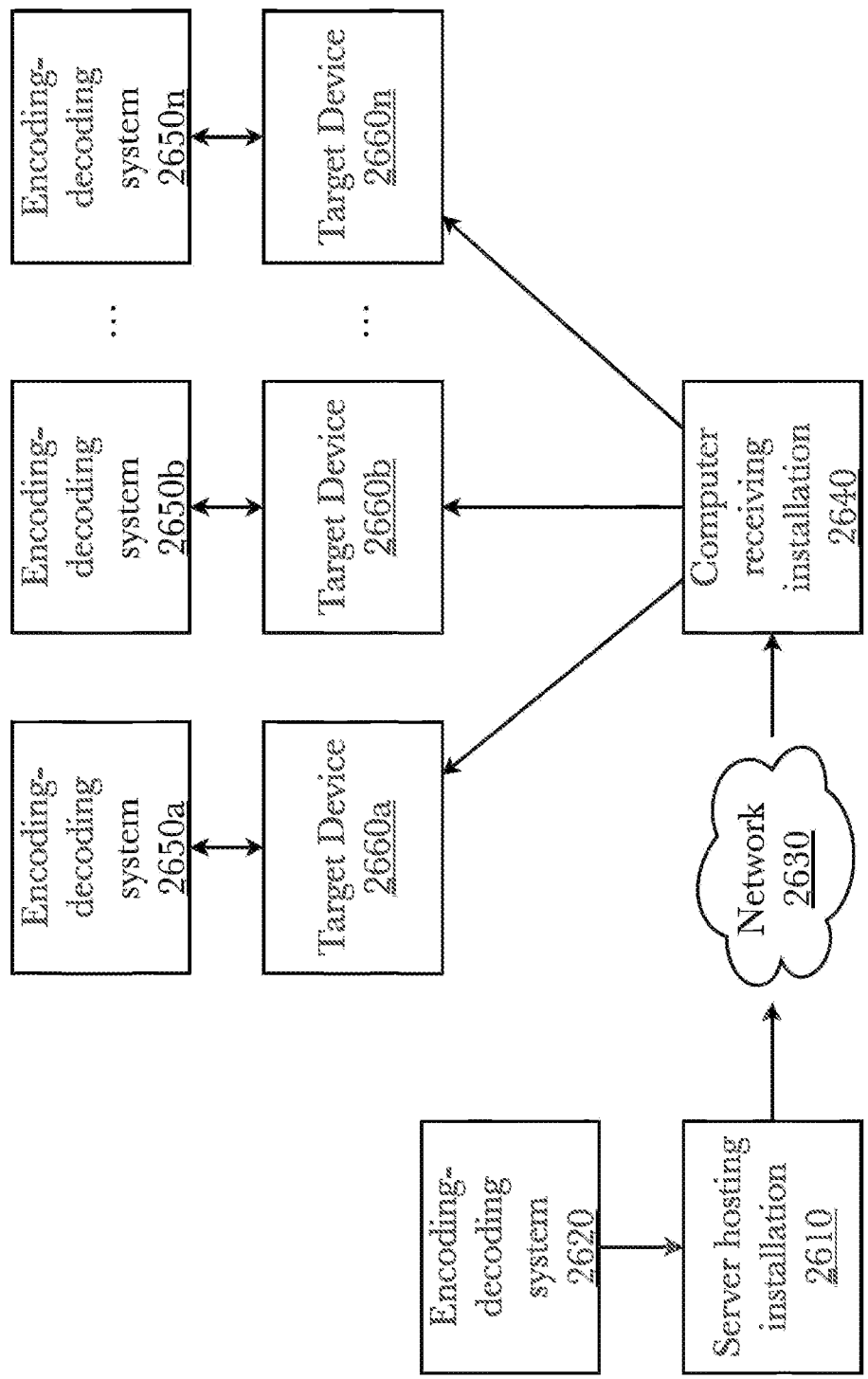
FIG. 26 is an exemplary system architecture of a data encoding system used for large-scale software installation such as operating systems.

FIG. 26 is an exemplary system architecture of a data encoding system used for large-scale software installation such as operating systems. Large-scale software installations typically require very large, but infrequent, file transfers. A server which hosts an installable software 2610 may host an encoding-decoding system 2620, allowing for data to be encoded into, and decoded from, sourceblocks or codewords, as disclosed in previous figures. The files for the large scale software installation are hosted on the server 2610, which is connected over a network 2630 to a recipient computer 2640. In this instance, the encoding and decoding system 2650a-n is stored on or connected to one or more target devices 2660a-n, along with a codebook or library of reference codes that the hosting server 2610 shares. The software is retrieved from storage at the hosting server 2610 in the form of codewords, and transferred over the network 2630 in the form of codewords to the receiving computer 2640. However, instead of being reconstructed at the receiving computer 2640, the codewords are transmitted to one or more target computing devices, and reconstructed and installed directly on the target devices 2660a-n. In this way, a far smaller file size, and smaller total update size, may be sent over a network or transferred between computing devices, even where the network 2630 between the receiving computer 2640 and target devices 2660a-n is low bandwidth, or where there are many target devices 2660a-n.

Figure 34:
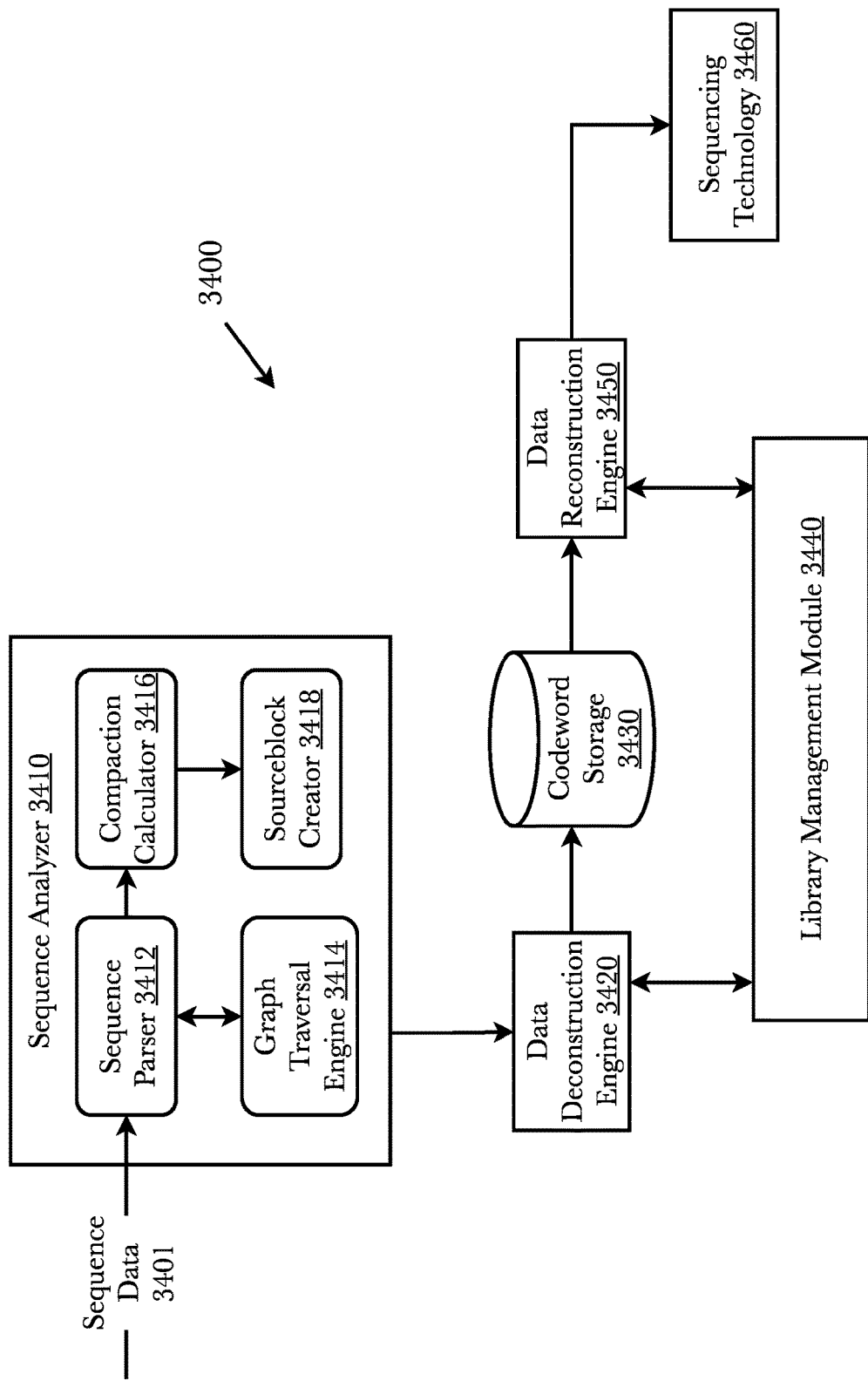
FIG. 34 is a block diagram illustrating an exemplary system architecture for a high-bandwidth encoding of genomic data system, according to various embodiments.

FIG. 34 is a block diagram illustrating an exemplary system architecture for a high-bandwidth encoding of genomic data system, according to various embodiments. According to an embodiment, the system 3400 may comprise a sequence analyzer 3410, a data deconstruction engine 3420, a codeword storage 3430 data store, a library management module 3440, and a data reconstruction engine 3450. In some embodiments of system 3400, sequencing module 3460 may be integrated with system 3400 such that outputted decoded sequence data from reconstruction engine 3450 may be fed directly into sequencing module 3460, which can comprise or make use of various sequencing technologies known in the art, at the location of a researcher or scientist. System 3400 may be configured to receive sequence data 3401 (e.g., genomic and/or bioinformatic data, etc.), scan the received sequence data to determine the amount of unique characters, indicate specific locations in sequence dataset 3401 where the character count increase, calculate and compare compaction ratios for different segments (i.e., sourceblocks), and optimally divide the received sequence data into a plurality of sourceblocks based on the results of the comparison. Then, data deconstruction engine 3420 may receive the sourceblocks, compacting and encoding each sourceblock with a reference code, and store the reference code and an indication of the location within the source sequence in which the encoded sourceblock is originally located as a codeword in codeword storage 3430. The result is the compaction, encryption, and storage or transmission of a very large genomic sequence dataset.

Systems and methods of the invention implement the encoding/decoding and compaction techniques previously described in this written description. In preferred embodiments, the data compaction technique is implemented for bioinformatic data. Bioinformatic data may be particularly well-suited to the encoding and compaction technique because such data: is often generated over small alphabets (i.e., the total group of characters found within a sequence dataset to be encoded); often contains many repetitive sequences; and is often very large (e.g., gigabyte, terabyte, etc.). The encoding and compaction techniques described herein exploit those features to create a compaction method that, though applicable to any kind of data, is particularly effective in compacting and encrypting bioinformatic data (e.g., sequence datasets).

The codewords stored in codeword storage 3420 are the compacted and encoded form of the received sequence dataset, providing data security and high levels of data compaction which greatly reduces the storage capacity required to store large amounts of sequence data, such as genomic sequences. Additionally, data reconstruction engine 3450 may be present which can receive codewords, decode the received codewords, and reconstruct the decoded sequence dataset back into its original format without loss of data. As both data deconstruction engine 3420 and data reconstruction engine 3450 have access to a same reference codebook which contains a plurality of codeword pairs, each codeword pair comprising a sequence data sourceblock and its corresponding reference code (and, in some embodiments, information about the location of the reference code within the sequence dataset), only codewords need be transmitted between the two engines at different locations, resulting in less bandwidth being required to transmit large sequence datasets.

Present in this embodiment, is a sequence analyzer 3410 which is configured to perform a variety of functions in order to prepare a received sequence dataset for further processing by data deconstruction engine 3420. The encoding and decoding system and methods described herein are applicable to a variety of formats of sequence data and genomic data such as an organism's genome, a multiple sequence alignment, a set of sequence read data, or a directed graph representing relationships among multiple genomic sequences. In some embodiments, the sequence or genomic data that is encoded comprises a graph representing at least a portion of a plurality of genomes. Since system 3400 may be applied to very large datasets, such as sequence reads, sequence alignments, or genomic reference graphs, very large genomic datasets may be encoded very compactly.

According to some embodiments, sequence analyzer 3410 may comprise a sequence parser 3412 configured to parse the sequence dataset to identify the format of the dataset. The format of the sequence dataset may be a text file (e.g., word document), a comma separated variable (CSV) format, a graphical format, a FASTA format, or other file format for storing genomic data known to those skilled in the art. Sequence parser 3412 may determine what type of file is received by analyzing the received datasets binaries and/or actual code, and may make use of a database (not shown) of basic file type definitions which are used to encode files into a particular file format. If the received sequence dataset is determined to be a non-graphical format, then the sequence dataset may be scanned through in its entirety in order to determine the number of unique characters contained within the sequence dataset. System 3400 may maintain a count of the number of unique characters found within a received dataset, iterating through a dataset and increasing a character count value each time a unique (that is, previously unencountered during the scan) character is encountered. This character count represents the size of the alphabet associated with received sequence dataset and may be used by system 3400 in order to determine locations in the sequence dataset where the number of unique characters increase by a power of two. These positions where the unique character count increases may be selected by system 3400 as the location in the dataset where division into a plurality of sourceblocks would result in efficient data compaction.

Once a received sequence dataset has been scanned resulting in a unique character count and an indication to the locations where the unique character count has increased by a power of two, compaction calculator 3416 may then calculate the compaction ratio that would be obtained by dividing the sequence data into one of the plurality of sourceblocks at one of the indicated positions that result in the best compaction ratio. Once the most efficient positions have been determined, a sourceblock creator 3418 may receive the sequence dataset 3401 and optimally deconstruct the sequence dataset into a plurality of sourceblocks at those positions. The plurality of sourceblocks may be sent to data deconstruction engine 3420 for compaction and encoding actions.

If the received sequence dataset is determined to be a graphical representation (e.g., DAG, bidirectional, etc.), then the sequence dataset can be sent to a graph traversal engine 3414 which may select, from a plurality of graph traversal algorithms, an appropriate graph traversal algorithm for the type of graph. Examples of graph traversal algorithms that may be stored and operable on the graph traversal engine 3414 may include, but are not limited to, depth-first search, breadth-first search, and greedy algorithm. In some embodiments, a breadth-first search algorithm may be set as the default graph traversal algorithm because it is used to visit all the nodes of a given graph. In this traversal algorithm, one node is selected and then all the adjacent nodes are visited one by one. After completing all of the adjacent vertices, it moves further to check another vertex and checks its adjacent vertices again. The selected (or default) graph traversal algorithm may be used to first identify the reference sequence (or reference node) associated with the sequence dataset. Once identified, the reference sequence is assigned a first index value, and all subsequent graph nodes are assigned an index value based on their relationship to the reference sequence. Due to the structure of graphs, graph traversal algorithms may visit the same vertex more than once. As each vertex in the graph is traversed, graph traversal engine 3414 may flag (or make use of some other signifier) each vertex as it is indexed in order to prevent the same vertex being indexed more than once. Indexing of vertices may be performed in such a way that a vertices that are connected by an edge may be assigned indexes close in value. For example, if vertex 1 is the reference sequence then it would be assigned index value 001, and it is connected to vertex 2, then vertex two would be assigned index value 002. The indexing of the graphical sequence data is necessary for capturing the topology of and the relationships contained within a genome graph. The assigned index value can be stored with the encoded sequence data (as part of the codeword), filling a similar role to the location indicator which is stored in the codebook created for non-graphical sequence datasets; as the index values can be used by data reconstruction engine 3450 to decode and reassemble the genomic graph data in the original format it was received in.

According to some embodiments, during a graph traversal operation as each node is traversed, sequence analyzer 3410 maintains a count of the unique characters contained within the genome graph, in a way similar described above with respect to sequence parser 3412. Nodes of the genome graph may be segmented based upon the unique character count and the indication of where the character count increase by a power of two. These segmentations may be sent to compaction calculator 3416, which may be configured to calculate and compare the compaction ratios associated with the received graph segmentations.

According to some embodiments, sequence analyzer 3410 may be configured to scan incoming sequence data to identify one or more points along the sequence at which the alphabet size will change and flags (or otherwise notes) those points at which the alphabet size will increase to a power of two (e.g., go from 3 to 4 or from 7 to 8). The powers of two are the relevant break-points for various embodiments of the disclosed system and method. Whenever one of these break-points is encountered by sequence analyzer 3410, compaction calculator 3416 calculates how much space it would take to encode the sequence with an alphabet of that size. The efficiency of the representation is then calculated, and these efficiency values can be compared against each other in order to determine the best alphabet size for a given region, thereby choosing break-points that optimize the compaction techniques. In some embodiments, these break-even points may be used to determine where and what size sourceblocks are to be selected and then sent to data deconstruction engine 3420 for compaction and encryption.

As an example of the above described break even points, consider this exemplary genomic sequence that can be processed by system 3400: NATGAC-GAGAGAGCA-TTTTTTT. This example is selected to illustrate different alphabet sizes that may be invoked with a particular division. The original genomic data is divided into three segments. The first segment includes NATGCA-. The second segment includes GAGAGAGCA-. The third segment includes TTTTTTT. The alphabet for the third segment is a single character ("T"). The alphabet for the for the first segment six characters (N, A, C, T, G, -) and thus requires 3 bits per character. The second segment has four characters and could be encoded using 2 bits per character. Once the data has been divided, it is ready to be encoded by data deconstruction engine 3420 as described throughout this disclosure.

Description of Method Aspects

Since the library consists of re-usable building sourceblocks, and the actual data is represented by reference codes to the library, the total storage space of a single set of data would be much smaller than conventional methods, wherein the data is stored in its entirety. The more data sets that are stored, the larger the library becomes, and the more data can be stored in reference code form.

As an analogy, imagine each data set as a collection of printed books that are only occasionally accessed. The amount of physical shelf space required to store many collections would be quite large, and is analogous to conventional methods of storing every single bit of data in every data set. Consider, however, storing all common elements within and across books in a single library, and storing the books as references codes to those common elements in that library. As a single book is added to the library, it will contain many repetitions of words and phrases. Instead of storing the whole words and phrases, they are added to a library, and given a reference code, and stored as reference codes. At this scale, some space savings may be achieved, but the reference codes will be on the order of the same size as the words themselves. As more books are added to the library, larger phrases, quotations, and other words patterns will become common among the books. The larger the word patterns, the smaller the reference codes will be in relation to them as not all possible word patterns will be used. As entire collections of books are added to the library, sentences, paragraphs, pages, or even whole books will become repetitive. There may be many duplicates of books within a collection and across multiple collections, many references and quotations from one book to another, and much common phraseology within books on particular subjects. If each unique page of a book is stored only once in a common library and given a reference code, then a book of 1,000 pages or more could be stored on a few printed pages as a string of codes referencing the proper full-sized pages in the common library. The physical space taken up by the books would be dramatically reduced. The more collections that are added, the greater the likelihood that phrases, paragraphs, pages, or entire books will already be in the library, and the more information in each collection of books can be stored in reference form. Accessing entire collections of books is then limited not by physical shelf space, but by the ability to reprint and recycle the books as needed for use.

The projected increase in storage capacity using the method herein described is primarily dependent on two factors: 1) the ratio of the number of bits in a block to the number of bits in the reference code, and 2) the amount of repetition in data being stored by the system.

With respect to the first factor, the number of bits used in the reference codes to the sourceblocks must be smaller than the number of bits in the sourceblocks themselves in order for any additional data storage capacity to be obtained. As a simple example, 16-bit sourceblocks would require 216, or 65536, unique reference codes to represent all possible patterns of bits. If all possible 65536 blocks patterns are utilized, then the reference code itself would also need to contain sixteen bits in order to refer to all possible 65,536 blocks patterns. In such case, there would be no storage savings. However, if only 16 of those block patterns are utilized, the reference code can be reduced to 4 bits in size, representing an effective compression of 4 times (16 bits/4 bits=4) versus conventional storage. Using a typical block size of 512 bytes, or 4,096 bits, the number of possible block patterns is 24,096, which for all practical purposes is unlimited. A typical hard drive contains one terabyte (TB) of physical storage capacity, which represents 1,953,125,000, or roughly 231, 512 byte blocks. Assuming that 1 TB of unique 512-byte sourceblocks were contained in the library, and that the reference code would thus need to be 31 bits long, the effective compression ratio for stored data would be on the order of 132 times (4,096/31≈132) that of conventional storage.

With respect to the second factor, in most cases it could be assumed that there would be sufficient repetition within a data set such that, when the data set is broken down into sourceblocks, its size within the library would be smaller than the original data. However, it is conceivable that the initial copy of a data set could require somewhat more storage space than the data stored in a conventional manner, if all or nearly all sourceblocks in that set were unique. For example, assuming that the reference codes are 1/10th the size of a full-sized copy, the first copy stored as sourceblocks in the library would need to be 1.1 megabytes (MB), (1 MB for the complete set of full-sized sourceblocks in the library and 0.1 MB for the reference codes). However, since the sourceblocks stored in the library are universal, the more duplicate copies of something you save, the greater efficiency versus conventional storage methods. Conventionally, storing 10 copies of the same data requires 10 times the storage space of a single copy. For example, ten copies of a 1 MB file would take up 10 MB of storage space. However, using the method described herein, only a single full-sized copy is stored, and subsequent copies are stored as reference codes. Each additional copy takes up only a fraction of the space of the full-sized copy. For example, again assuming that the reference codes are 1/10th the size of the full-size copy, ten copies of a 1 MB file would take up only 2 MB of space (1 MB for the full-sized copy, and 0.1 MB each for ten sets of reference codes). The larger the library, the more likely that part or all of incoming data will duplicate sourceblocks already existing in the library.

The size of the library could be reduced in a manner similar to storage of data. Where sourceblocks differ from each other only by a certain number of bits, instead of storing a new sourceblock that is very similar to one already existing in the library, the new sourceblock could be represented as a reference code to the existing sourceblock, plus information about which bits in the new block differ from the existing block. For example, in the case where 512 byte sourceblocks are being used, if the system receives a new sourceblock that differs by only one bit from a sourceblock already existing in the library, instead of storing a new 512 byte sourceblock, the new sourceblock could be stored as a reference code to the existing sourceblock, plus a reference to the bit that differs. Storing the new sourceblock as a reference code plus changes would require only a few bytes of physical storage space versus the 512 bytes that a full sourceblock would require. The algorithm could be optimized to store new sourceblocks in this reference code plus changes form unless the changes portion is large enough that it is more efficient to store a new, full sourceblock.

It will be understood by one skilled in the art that transfer and synchronization of data would be increased to the same extent as for storage. By transferring or synchronizing reference codes instead of full-sized data, the bandwidth requirements for both types of operations are dramatically reduced.

In addition, the method described herein is inherently a form of encryption. When the data is converted from its full form to reference codes, none of the original data is contained in the reference codes. Without access to the library of sourceblocks, it would be impossible to re-construct any portion of the data from the reference codes. This inherent property of the method described herein could obviate the need for traditional encryption algorithms, thereby offsetting most or all of the computational cost of conversion of data back and forth to reference codes. In theory, the method described herein should not utilize any additional computing power beyond traditional storage using encryption algorithms. Alternatively, the method described herein could be in addition to other encryption algorithms to increase data security even further.

In other embodiments, additional security features could be added, such as: creating a proprietary library of sourceblocks for proprietary networks, physical separation of the reference codes from the library of sourceblocks, storage of the library of sourceblocks on a removable device to enable easy physical separation of the library and reference codes from any network, and incorporation of proprietary sequences of how sourceblocks are read and the data reassembled.

Figure 7:
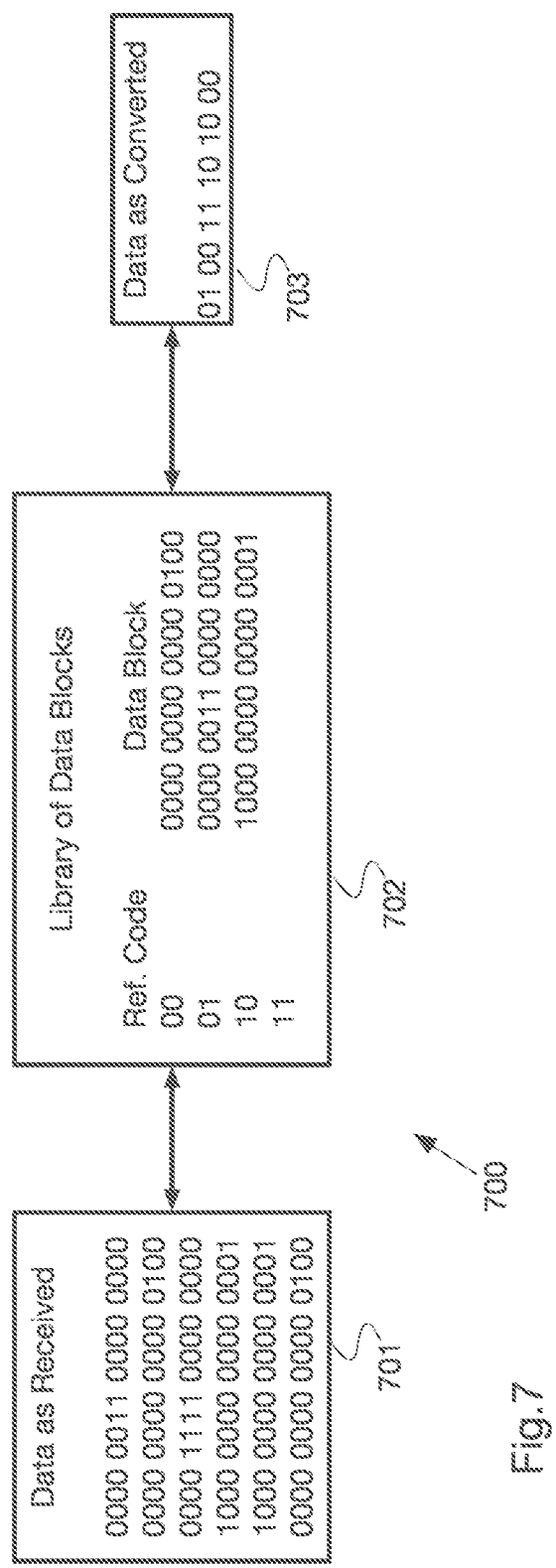
FIG. 7 is a diagram showing an example of how data might be converted into reference codes using an aspect of an embodiment.

FIG. 7 is a diagram showing an example of how data might be converted into reference codes using an aspect of an embodiment 700. As data is received 701, it is read by the processor in sourceblocks of a size dynamically determined by the previously disclosed sourceblock size optimizer 410. In this example, each sourceblock is 16 bits in length, and the library 702 initially contains three sourceblocks with reference codes 00, 01, and 10. The entry for reference code 11 is initially empty. As each 16 bit sourceblock is received, it is compared with the library. If that sourceblock is already contained in the library, it is assigned the corresponding reference code. So, for example, as the first line of data (0000 0011 0000 0000) is received, it is assigned the reference code (01) associated with that sourceblock in the library. If that sourceblock is not already contained in the library, as is the case with the third line of data (0000 1111 0000 0000) received in the example, that sourceblock is added to the library and assigned a reference code, in this case 11. The data is thus converted 703 to a series of reference codes to sourceblocks in the library. The data is stored as a collection of codewords, each of which contains the reference code to a sourceblock and information about the location of the sourceblocks in the data set. Reconstructing the data is performed by reversing the process. Each stored reference code in a data collection is compared with the reference codes in the library, the corresponding sourceblock is read from the library, and the data is reconstructed into its original form.

Figure 8:
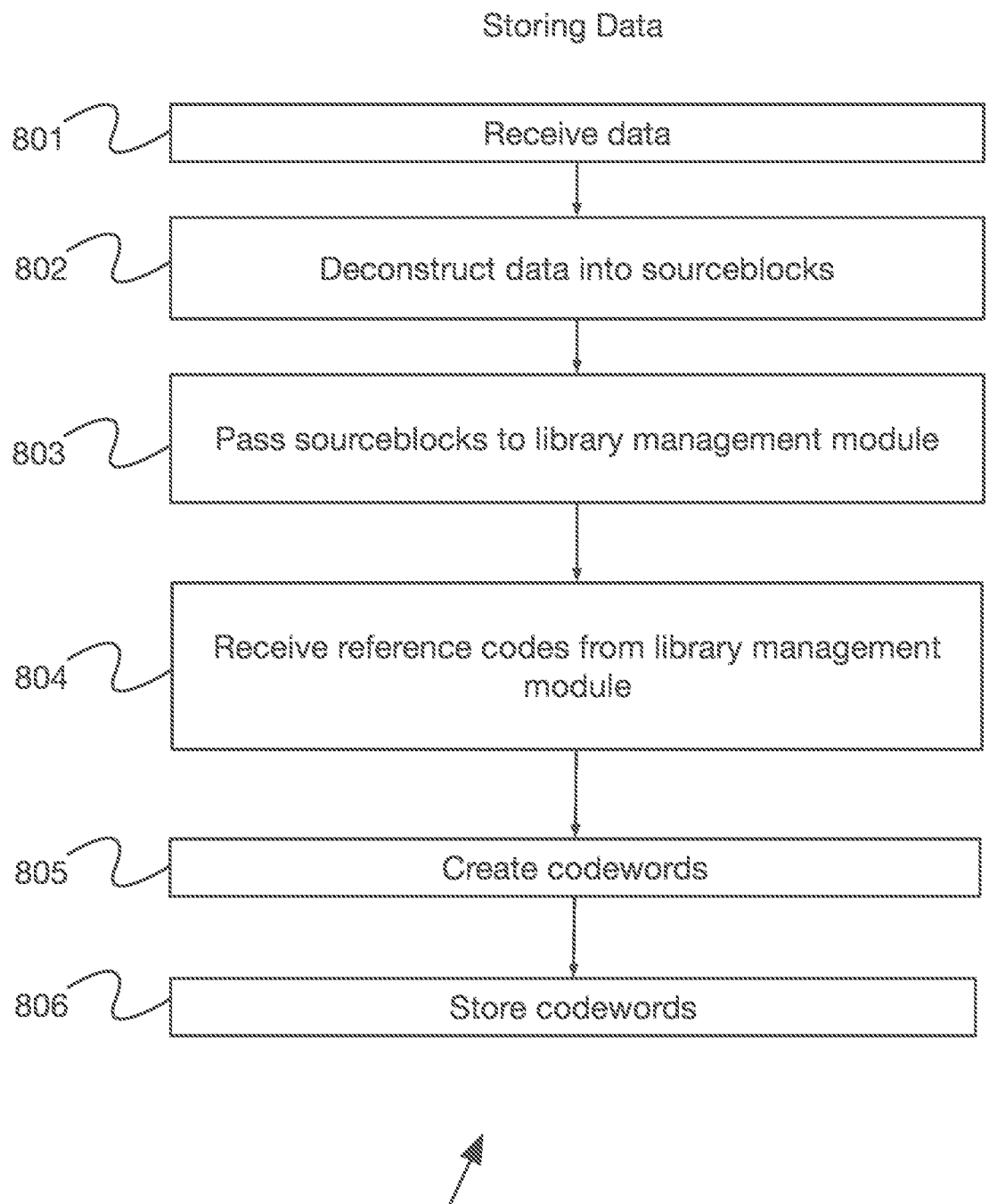
FIG. 8 is a method diagram showing the steps involved in using an embodiment to store data.

FIG. 8 is a method diagram showing the steps involved in using an embodiment 800 to store data. As data is received 801, it would be deconstructed into sourceblocks 802, and passed 803 to the library management module for processing. Reference codes would be received back 804 from the library management module, and could be combined with location information to create codewords 805, which would then be stored 806 as representations of the original data.

Figure 9:
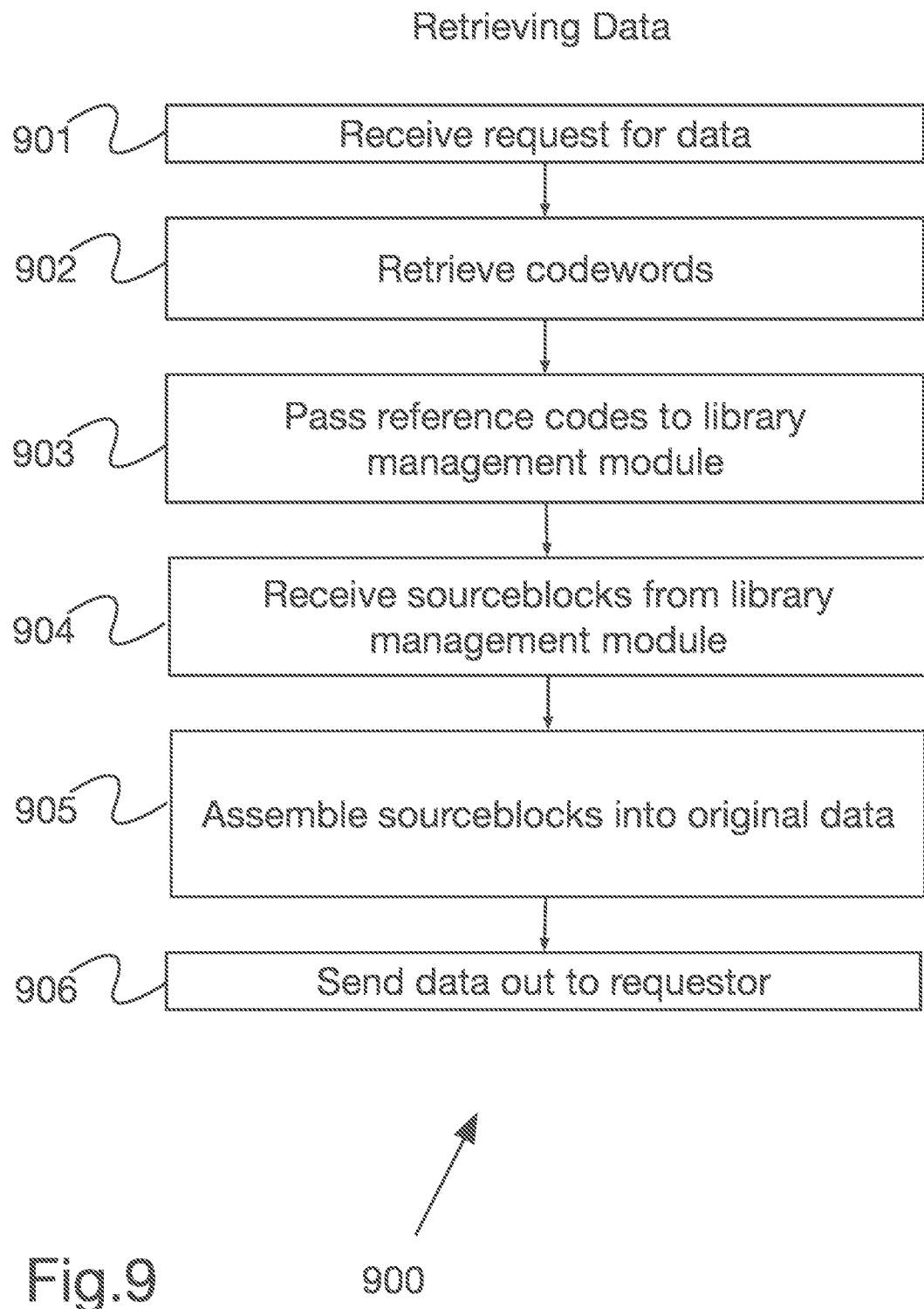
FIG. 9 is a method diagram showing the steps involved in using an embodiment to retrieve data.

FIG. 9 is a method diagram showing the steps involved in using an embodiment 900 to retrieve data. When a request for data is received 901, the associated codewords would be retrieved 902 from the library. The codewords would be passed 903 to the library management module, and the associated sourceblocks would be received back 904. Upon receipt, the sourceblocks would be assembled 905 into the original data using the location data contained in the codewords, and the reconstructed data would be sent out 906 to the requestor.

Figure 10:
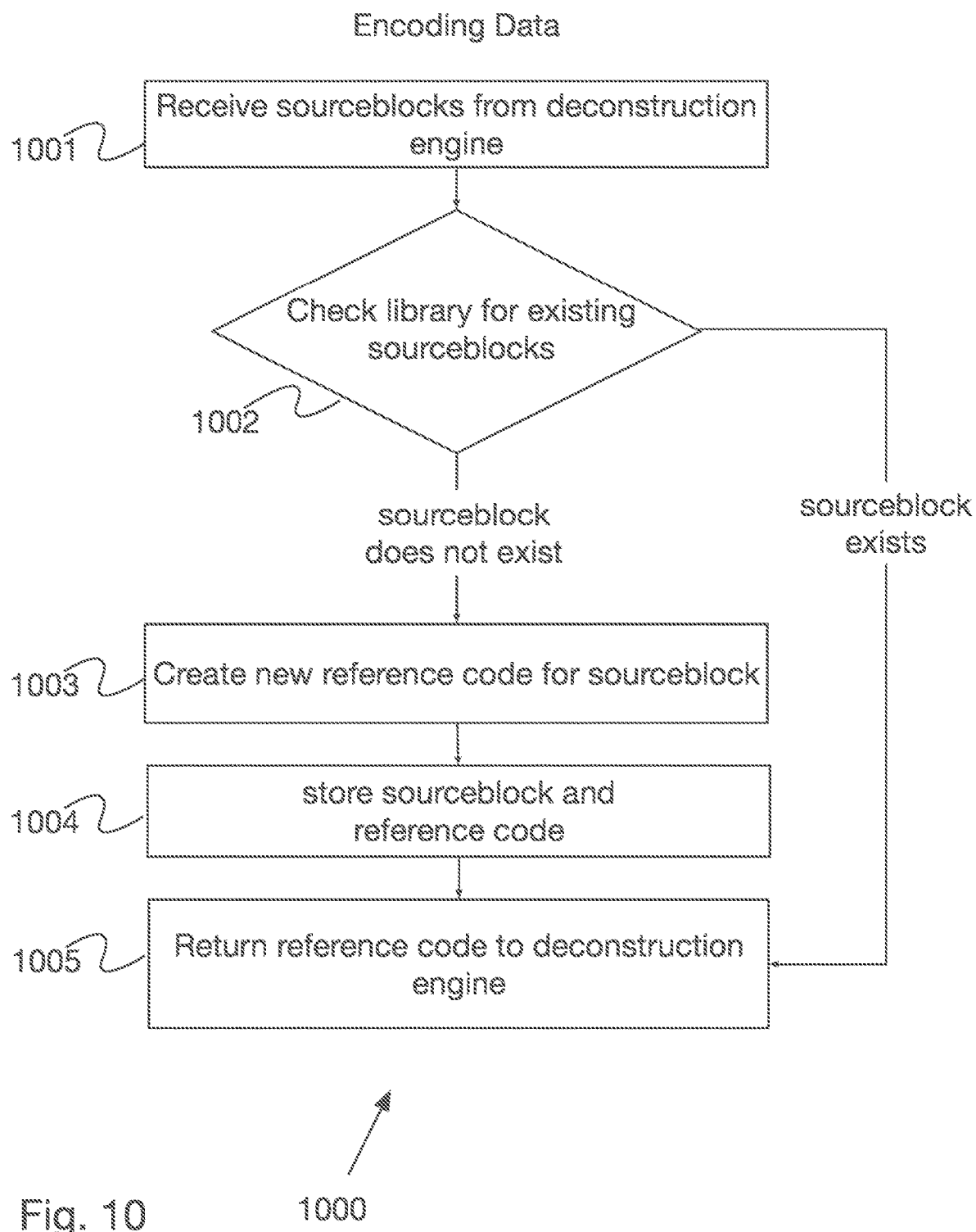
FIG. 10 is a method diagram showing the steps involved in using an embodiment to encode data.

FIG. 10 is a method diagram showing the steps involved in using an embodiment 1000 to encode data. As sourceblocks are received 1001 from the deconstruction engine, they would be compared 1002 with the sourceblocks already contained in the library. If that sourceblock already exists in the library, the associated reference code would be returned 1005 to the deconstruction engine. If the sourceblock does not already exist in the library, a new reference code would be created 1003 for the sourceblock. The new reference code and its associated sourceblock would be stored 1004 in the library, and the reference code would be returned to the deconstruction engine.

Figure 11:
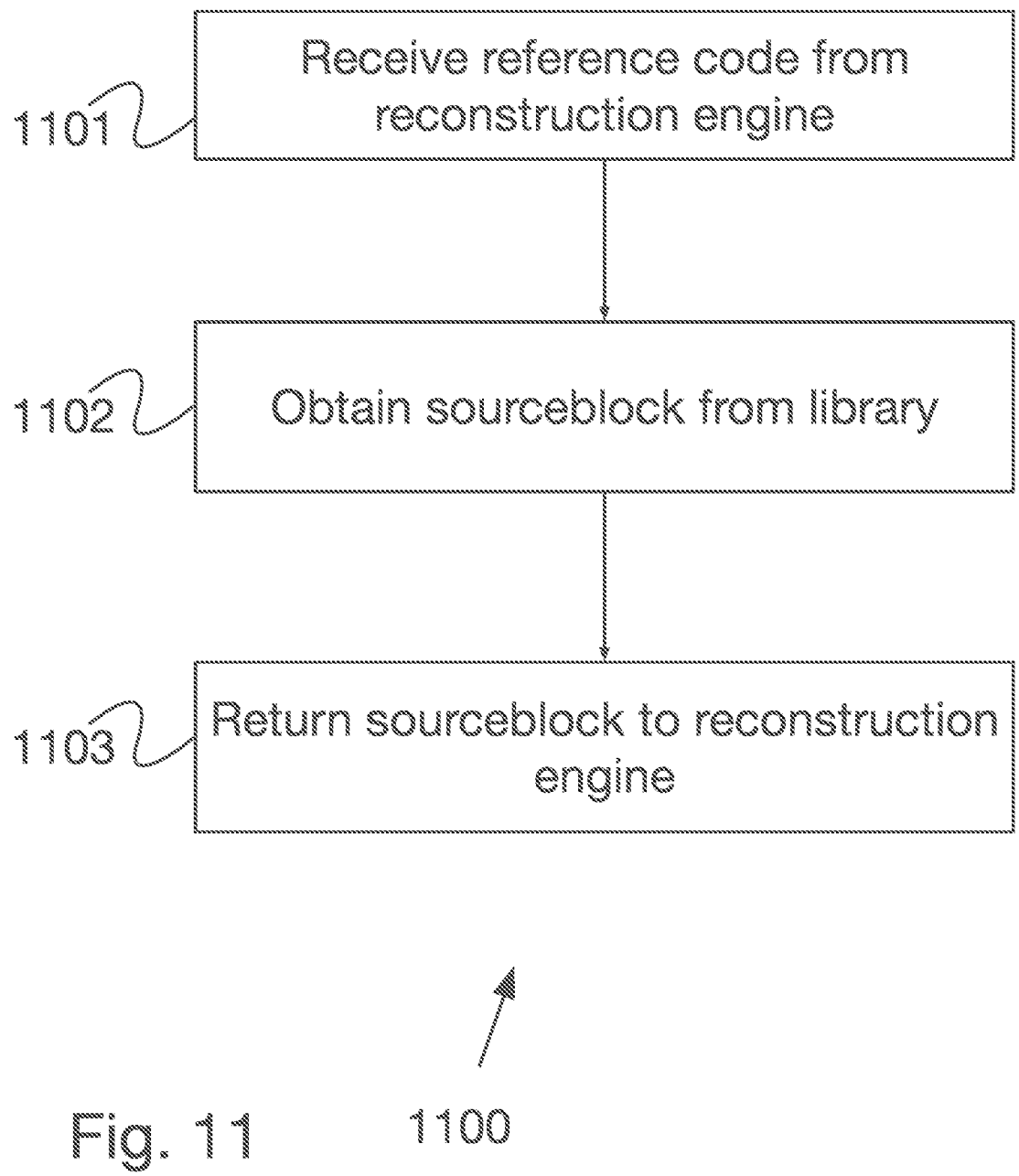
FIG. 11 is a method diagram showing the steps involved in using an embodiment to decode data.

FIG. 11 is a method diagram showing the steps involved in using an embodiment 1100 to decode data. As reference codes are received 1101 from the reconstruction engine, the associated sourceblocks are retrieved 1102 from the library, and returned 1103 to the reconstruction engine.

Figure 16:
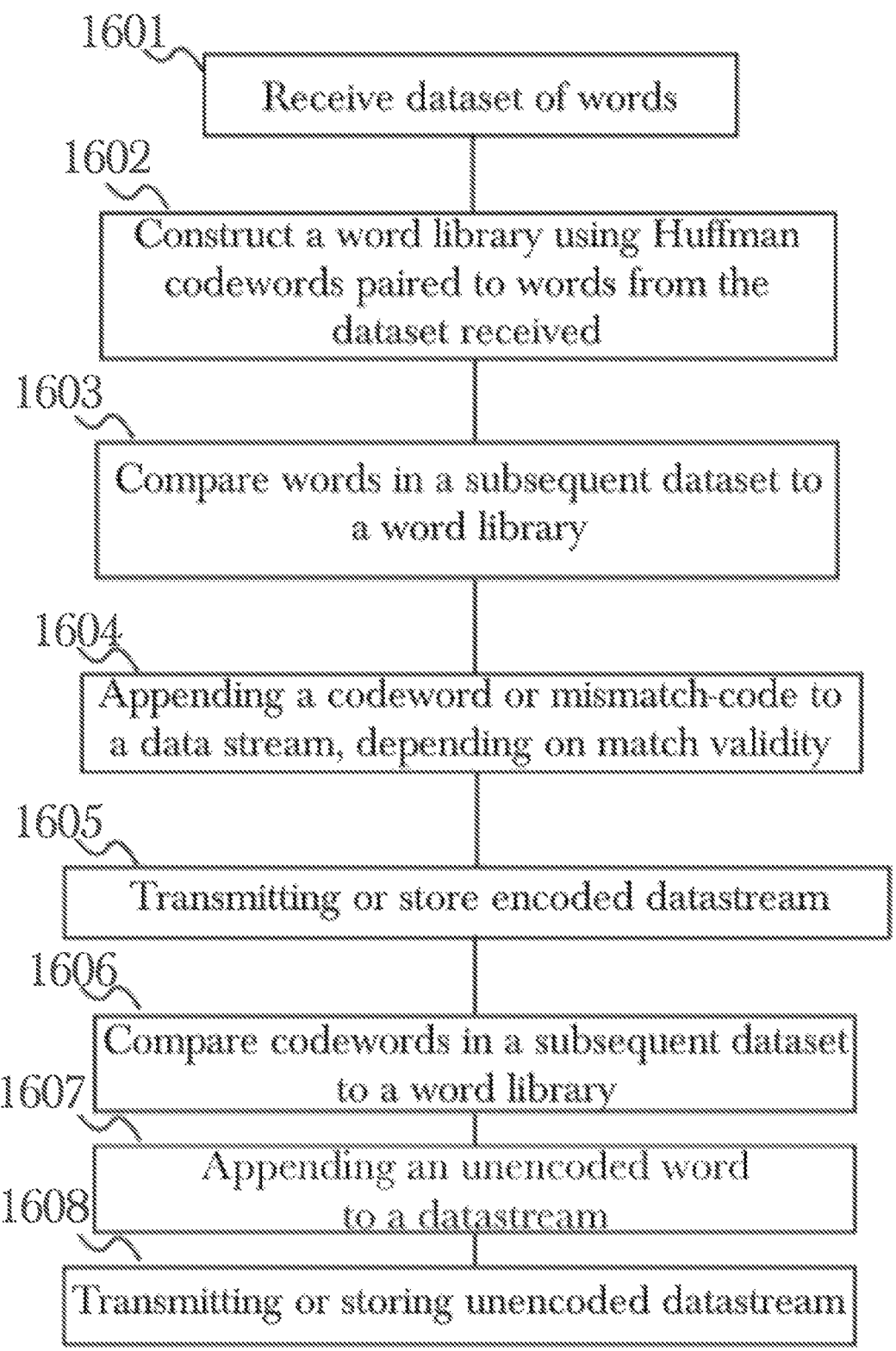
FIG. 16 is a method diagram illustrating key system functionality utilizing an encoder and decoder pair.

FIG. 16 is a method diagram illustrating key system functionality utilizing an encoder and decoder pair, according to a preferred embodiment. In a first step 1601, at least one incoming data set may be received at a customized library generator 1300 that then 1602 processes data to produce a customized word library 1201 comprising key-value pairs of data words (each comprising a string of bits) and their corresponding calculated binary Huffman codewords. A subsequent dataset may be received, and compared to the word library 1603 to determine the proper codewords to use in order to encode the dataset. Words in the dataset are checked against the word library and appropriate encodings are appended to a data stream 1604. If a word is mismatched within the word library and the dataset, meaning that it is present in the dataset but not the word library, then a mismatched code is appended, followed by the unencoded original word. If a word has a match within the word library, then the appropriate codeword in the word library is appended to the data stream. Such a data stream may then be stored or transmitted 1605 to a destination as desired. For the purposes of decoding, an already-encoded data stream may be received and compared 1606, and un-encoded words may be appended to a new data stream 1607 depending on word matches found between the encoded data stream and the word library that is present. A matching codeword that is found in a word library is replaced with the matching word and appended to a data stream, and a mismatch code found in a data stream is deleted and the following unencoded word is re-appended to a new data stream, the inverse of the process of encoding described earlier. Such a data stream may then be stored or transmitted 1608 as desired.

Figure 17:
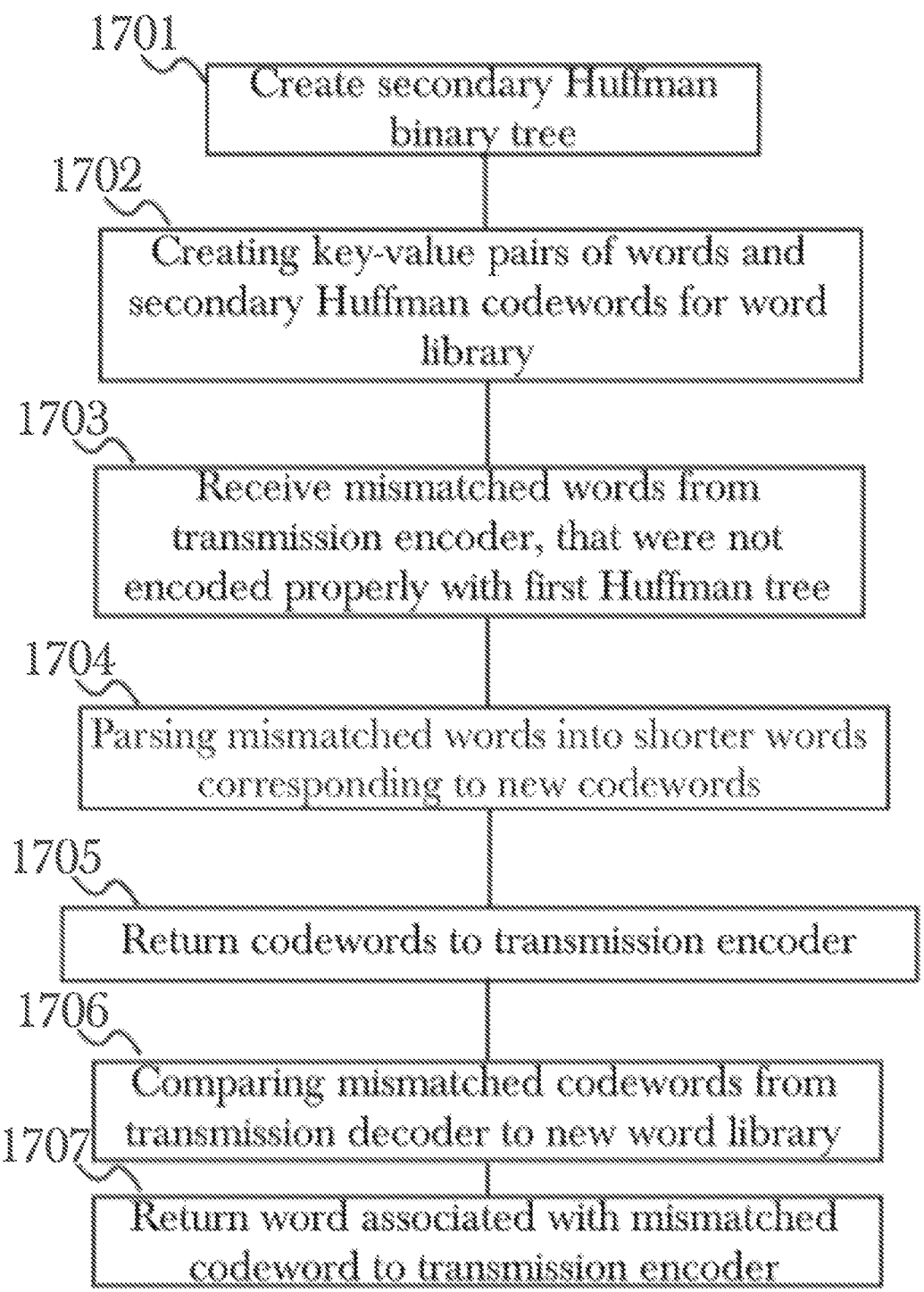
FIG. 17 is a method diagram illustrating possible use of a hybrid encoder/decoder to improve the compression ratio.

FIG. 17 is a method diagram illustrating possible use of a hybrid encoder/decoder to improve the compression ratio, according to a preferred aspect. A second Huffman binary tree may be created 1701, having a shorter maximum length of codewords than a first Huffman binary tree 1602, allowing a word library to be filled with every combination of codeword possible in this shorter Huffman binary tree 1702. A word library may be filled with these Huffman codewords and words from a dataset 1702, such that a hybrid encoder/decoder 1304, 1503 may receive any mismatched words from a dataset for which encoding has been attempted with a first Huffman binary tree 1703, 1604 and parse previously mismatched words into new partial codewords (that is, codewords that are each a substring of an original mismatched codeword) using the second Huffman binary tree 1704. In this way, an incomplete word library may be supplemented by a second word library. New codewords attained in this way may then be returned to a transmission encoder 1705, 1500. In the event that an encoded dataset is received for decoding, and there is a mismatch code indicating that additional coding is needed, a mismatch code may be removed and the unencoded word used to generate a new codeword as before 1706, so that a transmission encoder 1500 may have the word and newly generated codeword added to its word library 1707, to prevent further mismatching and errors in encoding and decoding.

It will be recognized by a person skilled in the art that the methods described herein can be applied to data in any form. For example, the method described herein could be used to store genetic data, which has four data units (e.g., its alphabet has four characters): C, G, A, and T. Those four data units can be represented as 2 bit sequences: 00, 01, 10, and 11, which can be processed and stored using the method described herein.

It will be recognized by a person skilled in the art that certain embodiments of the methods described herein may have uses other than data storage. For example, because the data is stored in reference code form, it cannot be reconstructed without the availability of the library of sourceblocks. This is effectively a form of encryption, which could be used for cyber security purposes. As another example, an embodiment of the method described herein could be used to store backup copies of data, provide for redundancy in the event of server failure, or provide additional security against cyberattacks by distributing multiple partial copies of the library among computers are various locations, ensuring that at least two copies of each sourceblock exist in different locations within the network.

Figure 18:
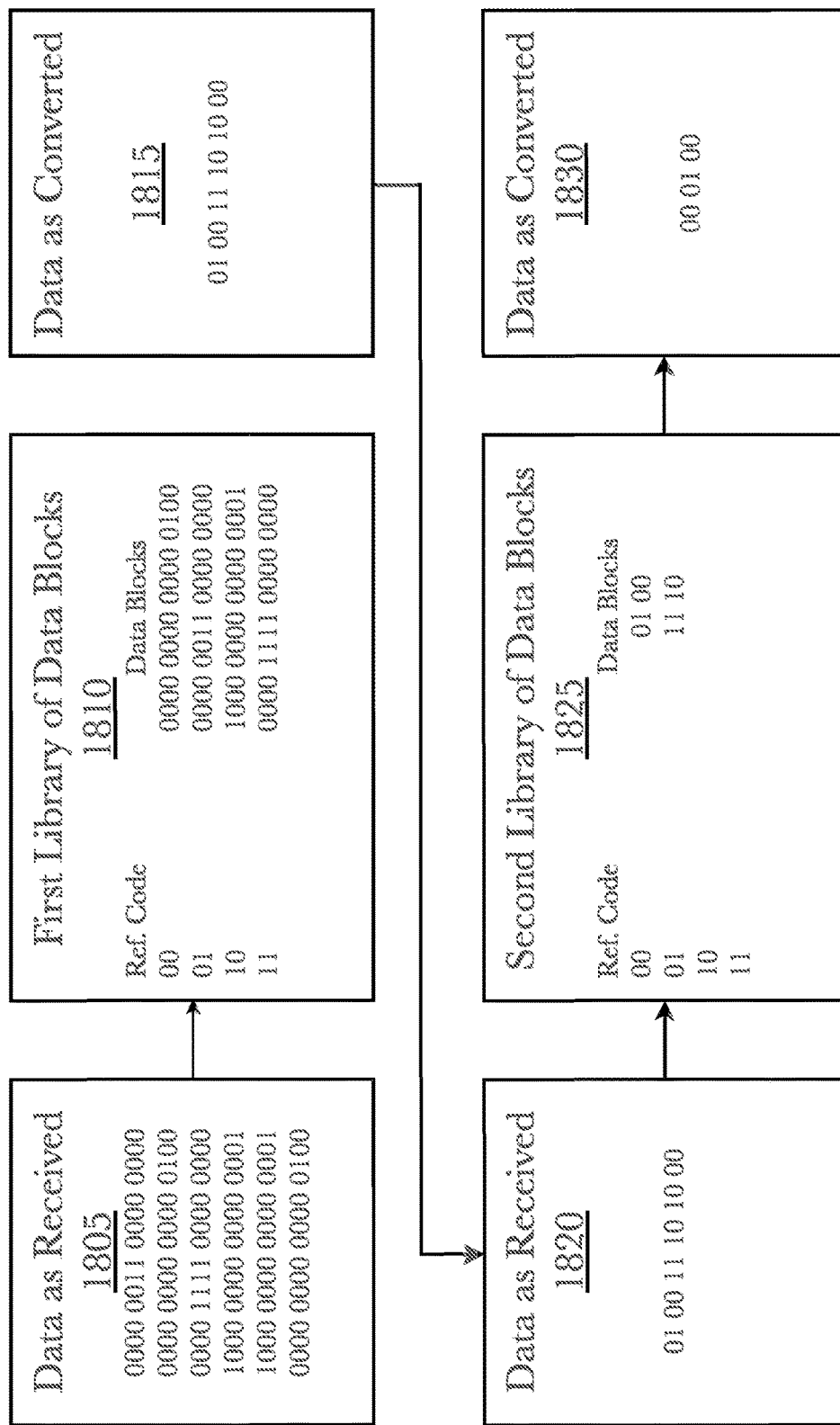
FIG. 18 is a flow diagram illustrating the use of a data encoding system used to recursively encode data to further reduce data size.

FIG. 18 is a flow diagram illustrating the use of a data encoding system used to recursively encode data to further reduce data size. Data may be input 1805 into a data deconstruction engine 102 to be deconstructed into code references, using a library of code references based on the input 1810. Such example data is shown in a converted, encoded format 1815, highly compressed, reducing the example data from 96 bits of data, to 12 bits of data, before sending this newly encoded data through the process again 1820, to be encoded by a second library 1825, reducing it even further. The newly converted data 1830 is shown as only 6 bits in this example, thus a size of 6.25% of the original data packet. With recursive encoding, then, it is possible and implemented in the system to achieve increasing compression ratios, using multi-layered encoding, through recursively encoding data. Both initial encoding libraries 1810 and subsequent libraries 1825 may be achieved through machine learning techniques to find optimal encoding patterns to reduce size, with the libraries being distributed to recipients prior to transfer of the actual encoded data, such that only the compressed data 1830 must be transferred or stored, allowing for smaller data footprints and bandwidth requirements. This process can be reversed to reconstruct the data. While this example shows only two levels of encoding, recursive encoding may be repeated any number of times. The number of levels of recursive encoding will depend on many factors, a non-exhaustive list of which includes the type of data being encoded, the size of the original data, the intended usage of the data, the number of instances of data being stored, and available storage space for codebooks and libraries. Additionally, recursive encoding can be applied not only to data to be stored or transmitted, but also to the codebooks and/or libraries, themselves. For example, many installations of different libraries could take up a substantial amount of storage space. Recursively encoding those different libraries to a single, universal library would dramatically reduce the amount of storage space required, and each different library could be reconstructed as necessary to reconstruct incoming streams of data.

Figure 20:
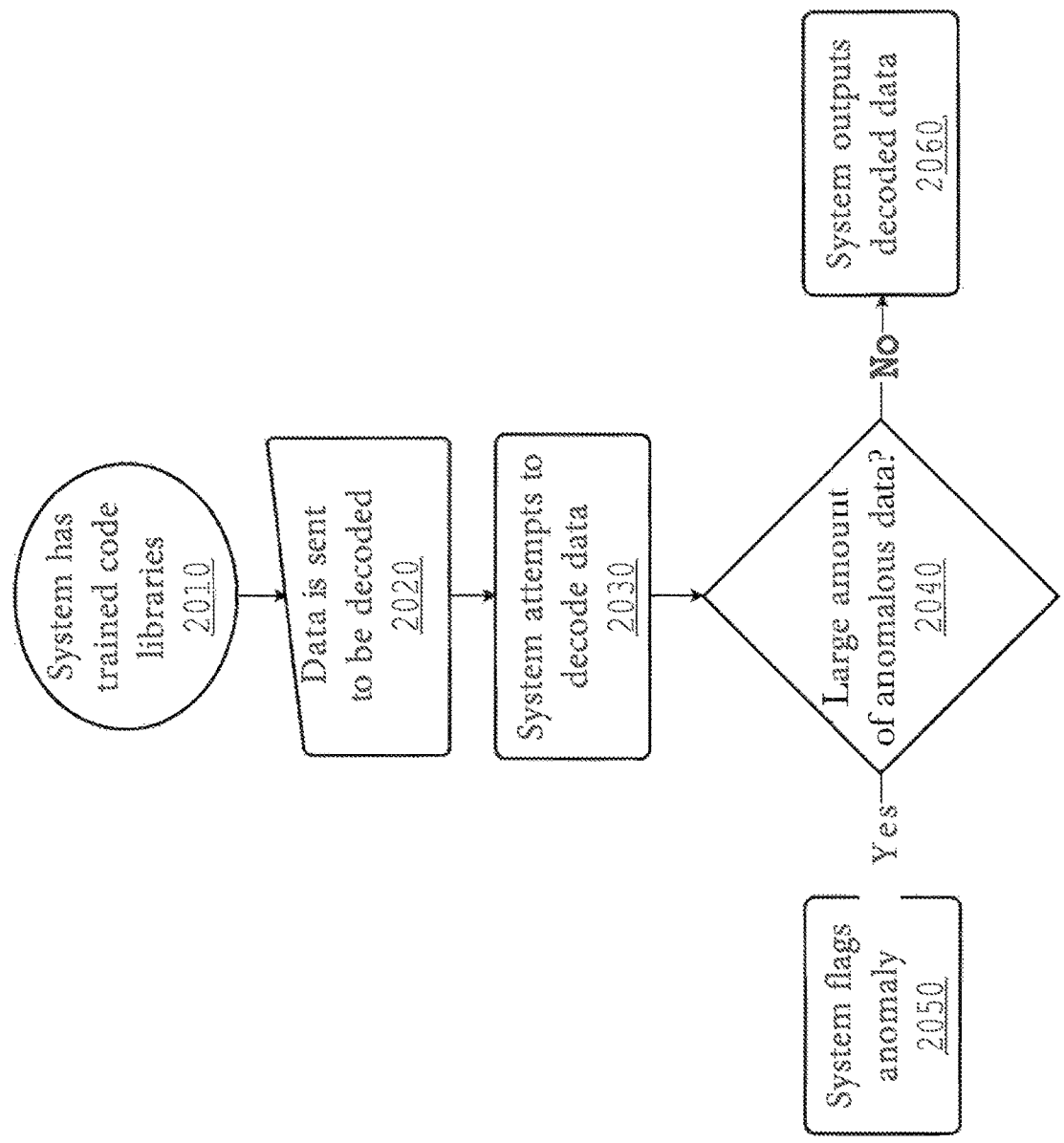
FIG. 20 is a flow diagram of an exemplary method used to detect anomalies in received encoded data and producing a warning.

FIG. 20 is a flow diagram of an exemplary method used to detect anomalies in received encoded data and producing a warning. A system may have trained encoding libraries 2010, before data is received from some source such as a network connected device or a locally connected device including USB connected devices, to be decoded 2020. Decoding in this context refers to the process of using the encoding libraries to take the received data and attempt to use encoded references to decode the data into its original source 2030, potentially more than once if recursive encoding was used, but not necessarily more than once. An anomaly detector 1910 may be configured to detect a large amount of un-encoded data 2040 in the midst of encoded data, by locating data or references that do not appear in the encoding libraries, indicating at least an anomaly, and potentially data tampering or faulty encoding libraries. A flag or warning is set by the system 2050, allowing a user to be warned at least of the presence of the anomaly and the characteristics of the anomaly. However, if a large amount of invalid references or unencoded data are not present in the encoded data that is attempting to be decoded, the data may be decoded and output as normal 2060, indicating no anomaly has been detected.

Figure 21:
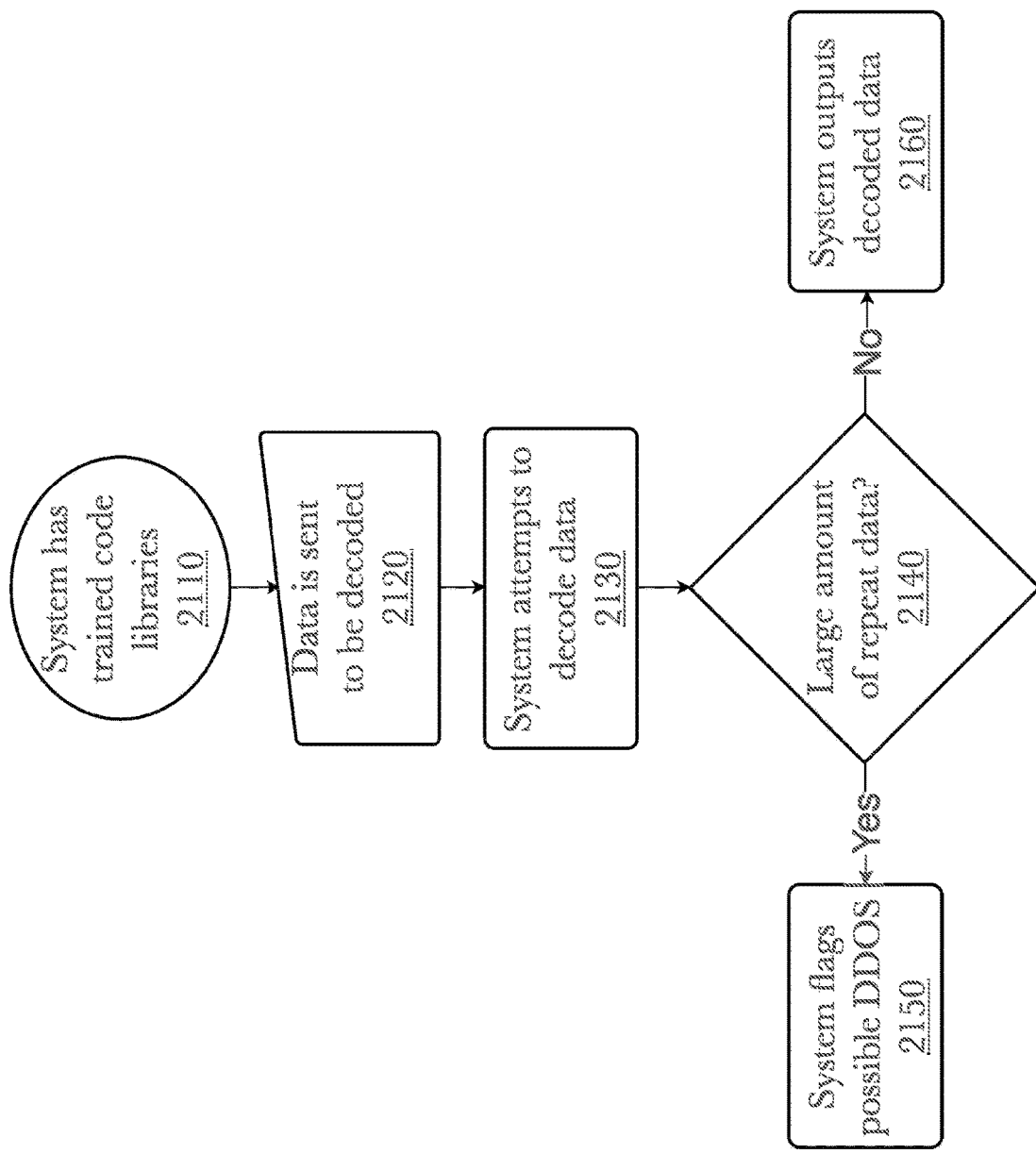
FIG. 21 is a flow diagram of a data encoding system used for Distributed Denial of Service (DDoS) attack denial.

FIG. 21 is a flow diagram of a method used for Distributed Denial of Service (DDoS) attack denial. A system may have trained encoding libraries 2110, before data is received from some source such as a network connected device or a locally connected device including USB connected devices, to be decoded 2120. Decoding in this context refers to the process of using the encoding libraries to take the received data and attempt to use encoded references to decode the data into its original source 2130, potentially more than once if recursive encoding was used, but not necessarily more than once. A DDoS detector 1920 may be configured to detect a large amount of repeating data 2140 in the encoded data, by locating data or references that repeat many times over (the number of which can be configured by a user or administrator as need be), indicating a possible DDoS attack. A flag or warning is set by the system 2150, allowing a user to be warned at least of the presence of a possible DDoS attack, including characteristics about the data and source that initiated the flag, allowing a user to then block incoming data from that source. However, if a large amount of repeat data in a short span of time is not detected, the data may be decoded and output as normal 2160, indicating no DDoS attack has been detected.

Figure 23:
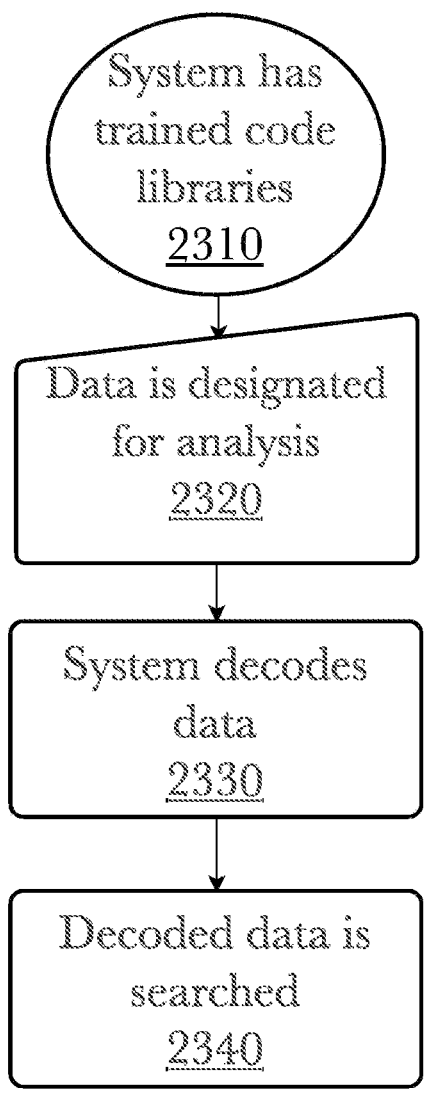
FIG. 23 is a flow diagram of an exemplary method used to enable high-speed data mining of repetitive data.

FIG. 23 is a flow diagram of an exemplary method used to enable high-speed data mining of repetitive data. A system may have trained encoding libraries 2310, before data is received from some source such as a network connected device or a locally connected device including USB connected devices, to be analyzed 2320 and decoded 2330. When determining data for analysis, users may select specific data to designate for decoding 2330, before running any data mining or analytics functions or software on the decoded data 2340. Rather than having traditional decryption and decompression operate over distributed drives, data can be regenerated immediately using the encoding libraries disclosed herein, as it is being searched. Using methods described in FIG. 9 and FIG. 11, data can be stored, retrieved, and decoded swiftly for searching, even across multiple devices, because the encoding library may be on each device. For example, if a group of servers host codewords relevant for data mining purposes, a single computer can request these codewords, and the codewords can be sent to the recipient swiftly over the bandwidth of their connection, allowing the recipient to locally decode the data for immediate evaluation and searching, rather than running slow, traditional decompression algorithms on data stored across multiple devices or transfer larger sums of data across limited bandwidth.

Figure 25:
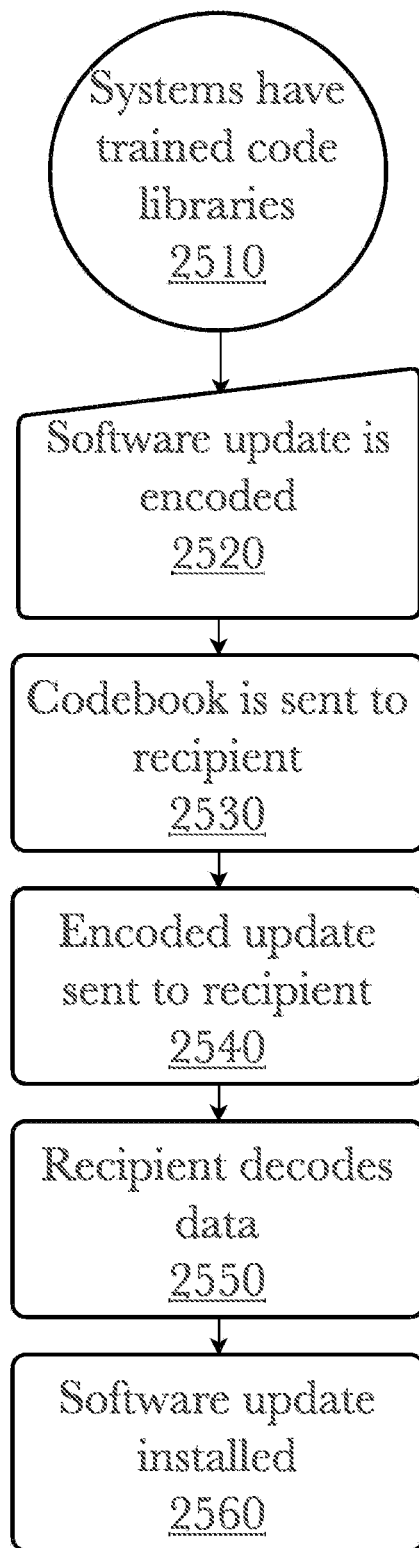
FIG. 25 is a flow diagram of an exemplary method used to encode and transfer software and firmware updates to a device for installation, for the purposes of reduced bandwidth consumption.

FIG. 25 is a flow diagram of an exemplary method used to encode and transfer software and firmware updates to a device for installation, for the purposes of reduced bandwidth consumption. A first system may have trained code libraries or "codebooks" present 2510, allowing for a software update of some manner to be encoded 2520. Such a software update may be a firmware update, operating system update, security patch, application patch or upgrade, or any other type of software update, patch, modification, or upgrade, affecting any computer system. A codebook for the patch must be distributed to a recipient 2530, which may be done beforehand and either over a network or through a local or physical connection, but must be accomplished at some point in the process before the update may be installed on the recipient device 2560. An update may then be distributed to a recipient device 2540, allowing a recipient with a codebook distributed to them 2530 to decode the update 2550 before installation 2560. In this way, an encoded and thus heavily compressed update may be sent to a recipient far quicker and with less bandwidth usage than traditional lossless compression methods for data, or when sending data in uncompressed formats. This especially may benefit large distributions of software and software updates, as with enterprises updating large numbers of devices at once.

Figure 27:
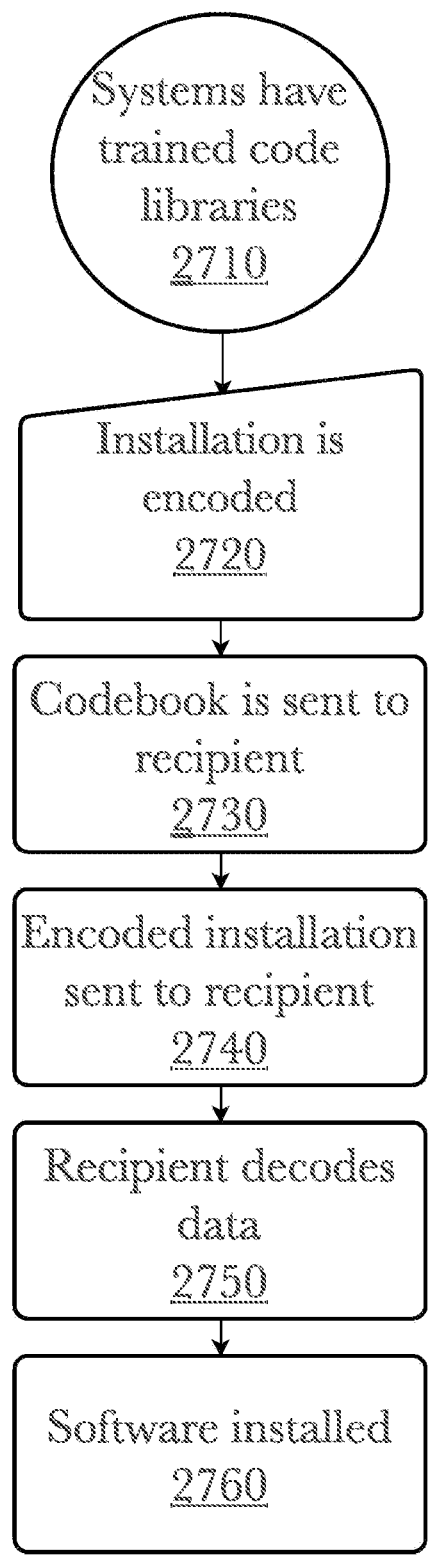
FIG. 27 is a flow diagram of an exemplary method used to encode new software and operating system installations for reduced bandwidth required for transference.

FIG. 27 is a flow diagram of an exemplary method used to encode new software and operating system installations for reduced bandwidth required for transference. A first system may have trained code libraries or "codebooks" present 2710, allowing for a software installation of some manner to be encoded 2720. Such a software installation may be a software update, operating system, security system, application, or any other type of software installation, execution, or acquisition, affecting a computer system. An encoding library or "codebook" for the installation must be distributed to a recipient 2730, which may be done beforehand and either over a network or through a local or physical connection, but must be accomplished at some point in the process before the installation can begin on the recipient device 2760. An installation may then be distributed to a recipient device 2740, allowing a recipient with a codebook distributed to them 2730 to decode the installation 2750 before executing the installation 2760. In this way, an encoded and thus heavily compressed software installation may be sent to a recipient far quicker and with less bandwidth usage than traditional lossless compression methods for data, or when sending data in uncompressed formats. This especially may benefit large distributions of software and software updates, as with enterprises updating large numbers of devices at once.

Figure 32:
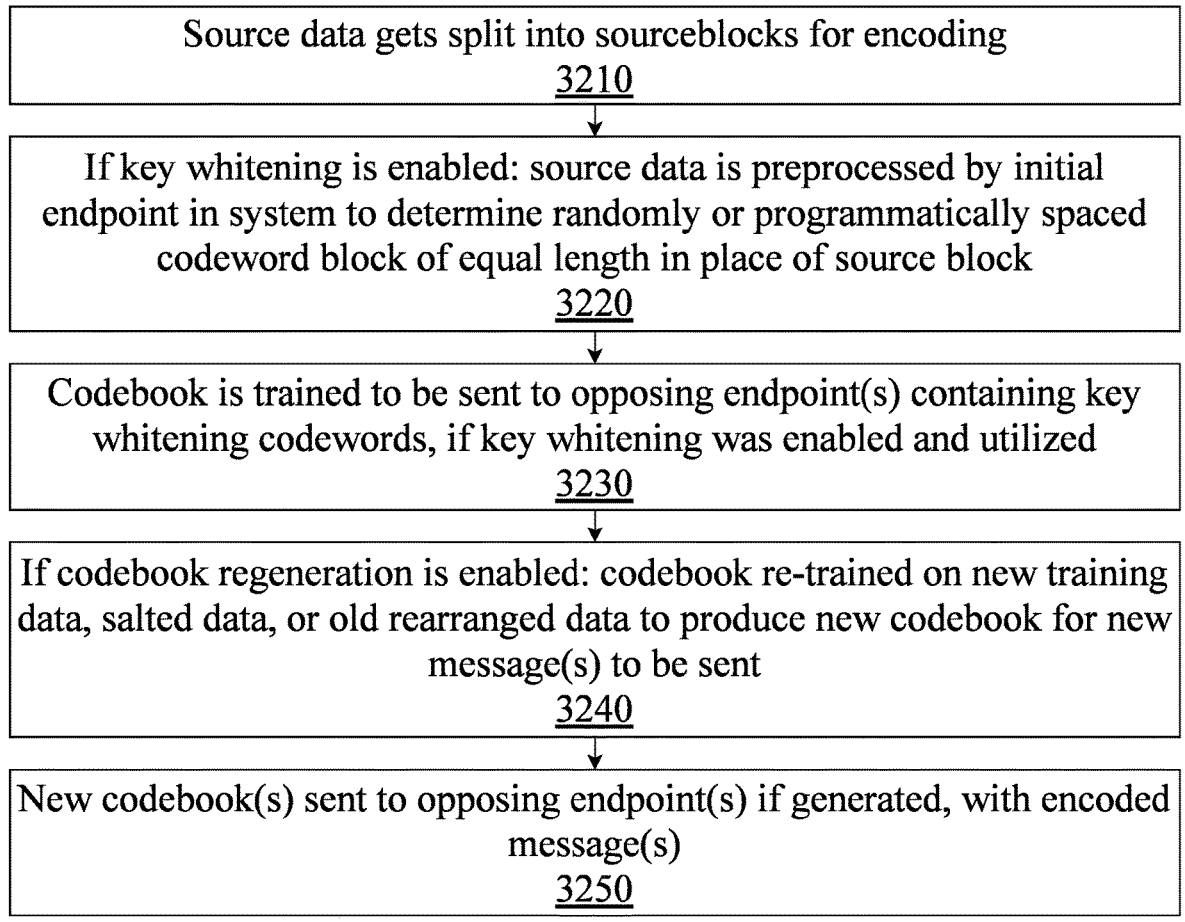
FIG. 32 is a method diagram illustrating a series of possible steps taken for further obfuscating a codebook and collection of source data between cryptographic endpoints, for increased hardness against intrusion or attack, according to an aspect.

FIG. 32 is a method diagram illustrating a series of possible steps taken for further obfuscating a codebook and collection of source data between cryptographic endpoints, for increased hardness against intrusion or attack, according to an aspect. First, source data must be split into blocks of source data, or "sourceblocks," for encoding 3210. This is a common first step for cryptographic block ciphers. The length of such blocks is paramount, as a block cipher switches sourceblocks of a given length for a codeword of equal length. A plurality of possible shuffling techniques may then be used on the source data, before or after being initially encrypted, depending on which steps are enabled by the encrypting endpoint. If key whitening is enabled, source data is preprocessed by the initial endpoint in system to determine randomly or programmatically spaced codeword blocks of equal length, in place of source blocks 3220, before encrypting the entire collection of blocks, effectively causing the randomly or programmatically selected blocks to become double or n encrypted, requiring multiple decrypting steps to recover the original source material. This key whitening may instead also be used for XOR encrypting, in which either the original sourceblock or a codeblock is sent in place of certain blocks, and the decrypting endpoint decrypts with the same XOR pattern, such that any given cipher block may have at least two (but possibly more) versions that may be used, making intrusion or attacking the encryption more difficult and costly, requiring the use of statistical models from the attackers.

"Key whitening" 3220 can be used to make attackers' task significantly harder, by preprocessing all data before transmission via XOR (meaning either the original data, or an alternative pre-processed cipher may be placed in its place, before the data is encrypted) with a previously agreed-upon random key whose length is an integer divisor of the sourceblock length. It need only be a divisor of a small multiple of the sourceblock length, where the increased size of this multiplying factor will increase the codebook size and introduce additional latency. The system may be insensate to the contents of sourceblocks, and instead rely solely on their frequencies. Thus, for example, if sourceblocks of length 64 are XOR-ed with a separate shared key of length 64 before training and also during encoding/decoding, attackers would have to use computationally expensive statistical attacks (or side-channel attacks, etc.) to obtain this key before the results of any codebook or key attacks could be used to obtain any unencrypted data. This preprocessing key may be updated regularly and communicated via public key encryption or a secure channel between sender and receiver in order to thwart attackers without large amounts of time or computing resources at their disposal.

The codebook may also trained to be sent to opposing endpoint(s) containing key whitening codewords, if key whitening was enabled and utilized 3230, causing the codebook or codebooks used to become regenerated in a different state than before, further complicating the task of attackers. If codebook regeneration is enabled in this way, the codebook may be re-trained on new training data, salted data, or old data that has merely bee rearranged, to produce a new codebook for new message(s) to be sent 3240 between the endpoints.

Because of the order-dependent and highly nonlinear nature of several subroutines of some learning processes, new sourceblock-codeword pair mappings may be very different each time a training process executes. These new codebooks, when pushed out to the transmitting and receiving devices 3250, serve as fresh keys, frustrating attackers whose time and resources cracking keys will be largely wasted with each codebook update. Similar to using key whitening as described above, this significantly increases the difficulty of extracting keys and plaintext in order to compromise the privacy/security of AtomBeam-encoded data.

Figure 33:
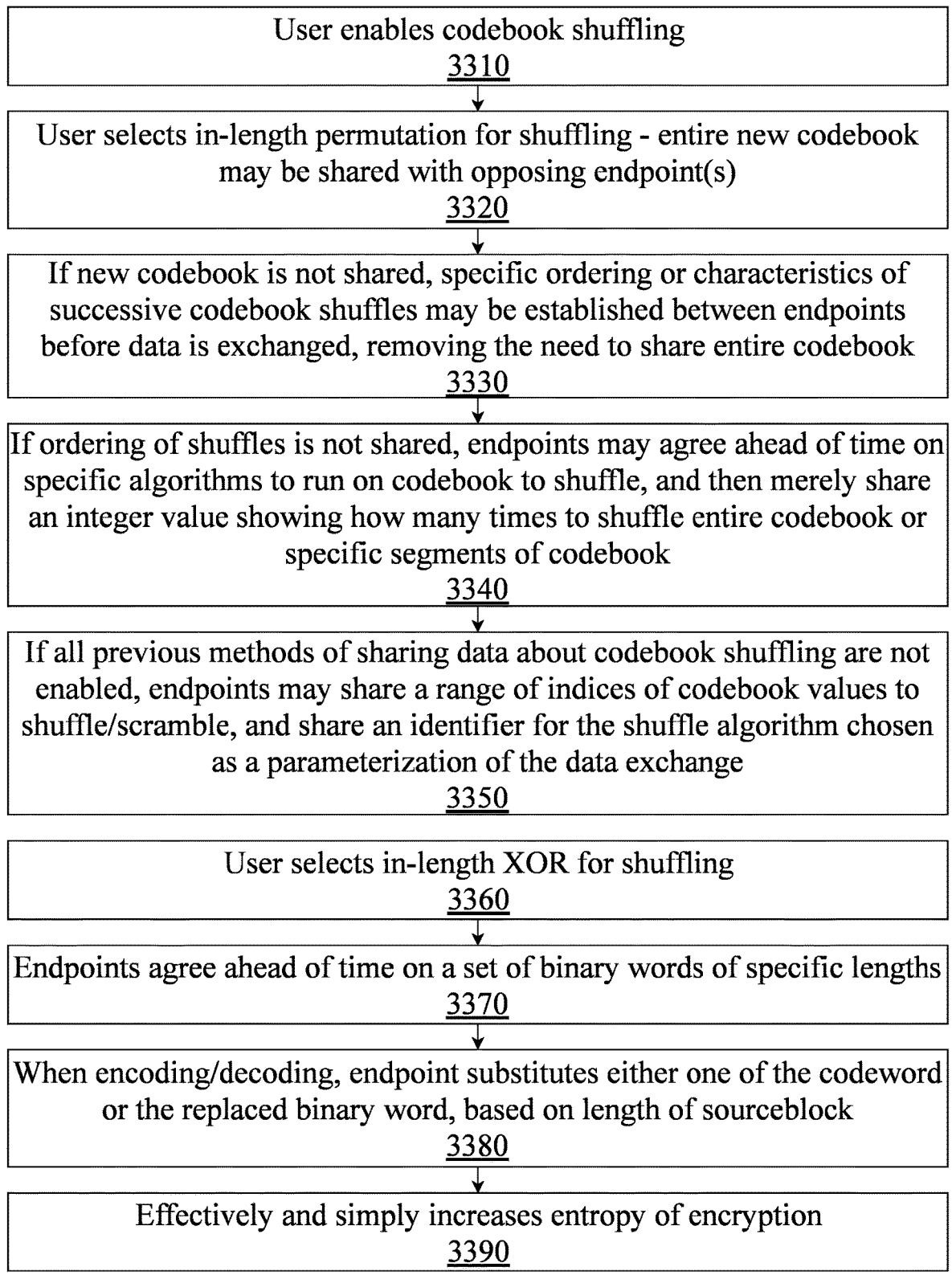
FIG. 33 is another method diagram illustrating a series of possible steps taken for further obfuscating a codebook and collection of source data between cryptographic endpoints, for increased hardness against intrusion or attack, according to an aspect.

FIG. 33 is another method diagram illustrating a series of possible steps taken for further obfuscating a codebook and collection of source data between cryptographic endpoints, for increased hardness against intrusion or attack, according to an aspect. First, a user such as the initial encrypting endpoint must enable codebook shuffling 3310, which may be enabled through a text or graphical user interface when using the encrypting system. The user may select two differing methods of codebook shuffling other than those previously disclosed, the first method being an in-length permutation for shuffling in which an entirely new codebook may be shared with the opposing endpoint or endpoints 3320.

All properties of the codebook, and the system that uses the codebook, are left unchanged if all codewords of a fixed length are permuted amongst themselves. Therefore, the sender and receiver would agree, perhaps via an encrypted communication, on one permutation per length when an update is triggered. That is, one endpoint (sender or receiver) will find the minimum codeword length m and the maximum codeword length M, then tally the number of codewords of each length: L(m), L(m+1), . . . , L(M). Then, it will generate a permutation by one of the methods described below for each such length: tau_m, tau_(m+1), . . . , tau_M, where tau_k is a function for a permutation of $\{1,2, \ldots, L(k)\}$, i.e. $\{tau\_k(1), \ldots, tau\_k(L(k))\}$ is a reordering of $\{1,2, \ldots, L(k)\}$. Then, the list of tau_j, j from m to M, may be securely transmitted to the other endpoint. The sender, when they use the codebook, will look up the sourceblock S in the codebook and find, for instance, that it is the "j-th" codeword of length L in the codebook, then transmit the tau_j(L) codeword among codewords of length L in the codebook. The receiver, upon receipt of this codeword, looks it up in the codebook and finds that it is, for instance, the "T-th" codeword among codewords of length L in the codebook, then may apply the inverse function of the tau's, i.e. find the codeword of length L numbered inverse_tau_L(T) in the codebook, which will correspond to the sourceblock S. There is also a way to do this less implicitly if the user can afford to store temporary codebooks instead of using these permutations at runtime: for each j and L, replace the j-th codeword of length L in the encoding codebook with the codeword numbered tau_L(j); in the decoding codebook, the T-th sourceblock corresponding to a codeword of length L is replaced with the sourceblock numbered inverse_tau_L(T). In this latter version, the decoding codebook must be accompanied by the list of tau's, or at least enough information to obtain the tau's, or else decoding will not be possible.

As part of this first method of shuffling using functions to replace specified codewords with alternatives, essentially utilizing a partial second-layer which is more difficult to attack than a full second-layer of encrypting since it is non-obvious which layer is which and which codewords are switched, several possible variations may exist.

If the new codebook is not shared or it is not desirable to share the new codebook, specific ordering or characteristics of successive codebook shuffles may be established between endpoints before data is exchanged, removing the need to share the entire codebook 3330, but decreasing the strength of the shuffle from outside intrusion due to a decrease in the entropy of the shuffling. Using this variation, a set of "R tau" functions for each valid length L are agreed upon at the beginning by the endpoints: tau_{L,1}, tau_{L,2}, . . . , tau_{L,R}. (R could vary between values of L.) Then, the endpoints agree with each shuffle update on indices i_m, i_(m+1), . . . , i_M (chosen randomly), and use tau_{L,i_L} for the length-L permutation. This is slightly less secure than generating new tau_k functions for each permutation, but requires much less data be computed and sent.

Alternatively, If ordering of shuffles is not shared, endpoints may agree ahead of time on specific algorithms to run on codebook to shuffle, and then merely share an integer value showing how many times to shuffle entire codebook or specific segments of codebook 3340. For instance, a set of tau's are agreed upon at the beginning by the endpoints, i.e. tau_m, tau_(m+1), . . . , tau_M. Then, the endpoints agree with each shuffle update on integers i_m, i_(m+1), . . . , i_M (chosen randomly), and use tau_L^(i_L) for the length-L permutation, where the exponent here denotes function self-composition. That is, tau^1(x)=tau, tau^2(x)=tau (tau(x)), tau^3(x)=tau(tau(tau(x))), etc. This is an even less secure than the previous option but requires even less data be sent.

If all previous methods of sharing data about codebook shuffling are not used, an alternative shuffle may involve endpoints sharing a range of indices of codebook values to shuffle/scramble, and share an identifier for the shuffle algorithm chosen as a parameterization of the data exchange 3350. For instance, a parametric recipe for tau's are agreed upon at the beginning by the endpoints: f_m(j), . . . , f_M(j), where f_r(j) is a permutation of $\{1, \ldots, L(r)\}$ for each j in some range of indices. Then, the endpoints agree with each shuffle update on indices i_m, ..., i_M (chosen randomly) and use the permutation tau_L=f_L(i_L) for each L to permute the length-L codewords. For example, f_L(j) may be a single previously agreed upon permutation rho_L plus j modulo L(r). For another example, f_L(j) may be multiplication modulo L(r) by the j-th invertible element of the ring of integers modulo L(r). There are an infinitude of such recipes possible which could use exponentiation in modular arithmetic, standard card shuffle permutations, permutations arising as the order type of the sequence of integer multiples of an irrational modulo 1, etc. This method requires transmitting and keeping track of the least amount of information, but adds the least amount of hardness to an intruder's interception task.

Alternatively, a different method of shuffling may be used, in which the user may select in-length XOR for shuffling 3360. The endpoints could agree on a set of binary words w_m, ..., w_M of length m, m+1, ..., M (see above for definitions of m and M) 3370. Then, upon receipt of the sourceblock S, the encoder obtains a codeword C of length L in the usual way, or in conjunction with the permutation shuffling mechanism in (a), then sends (C XOR w_L) 3380. The decoder, upon receiving C', computes (C' XOR w_L) (which will equal C), and then decodes it in the standard way. Again, codebooks can be stored in "XORed" version, but they must be accompanied by the binary words w_j to use them, or else the user must have enough information accompanying the codebook to locate the w_j for use (perhaps via a separate authenticated communication process). Without having the w_j binary words accompanied by the encrypted data transmission, this method may effectively and simply increase entropy of encryption 3390, making it harder for attackers or intruders to compromise the encryption.

Figure 35:
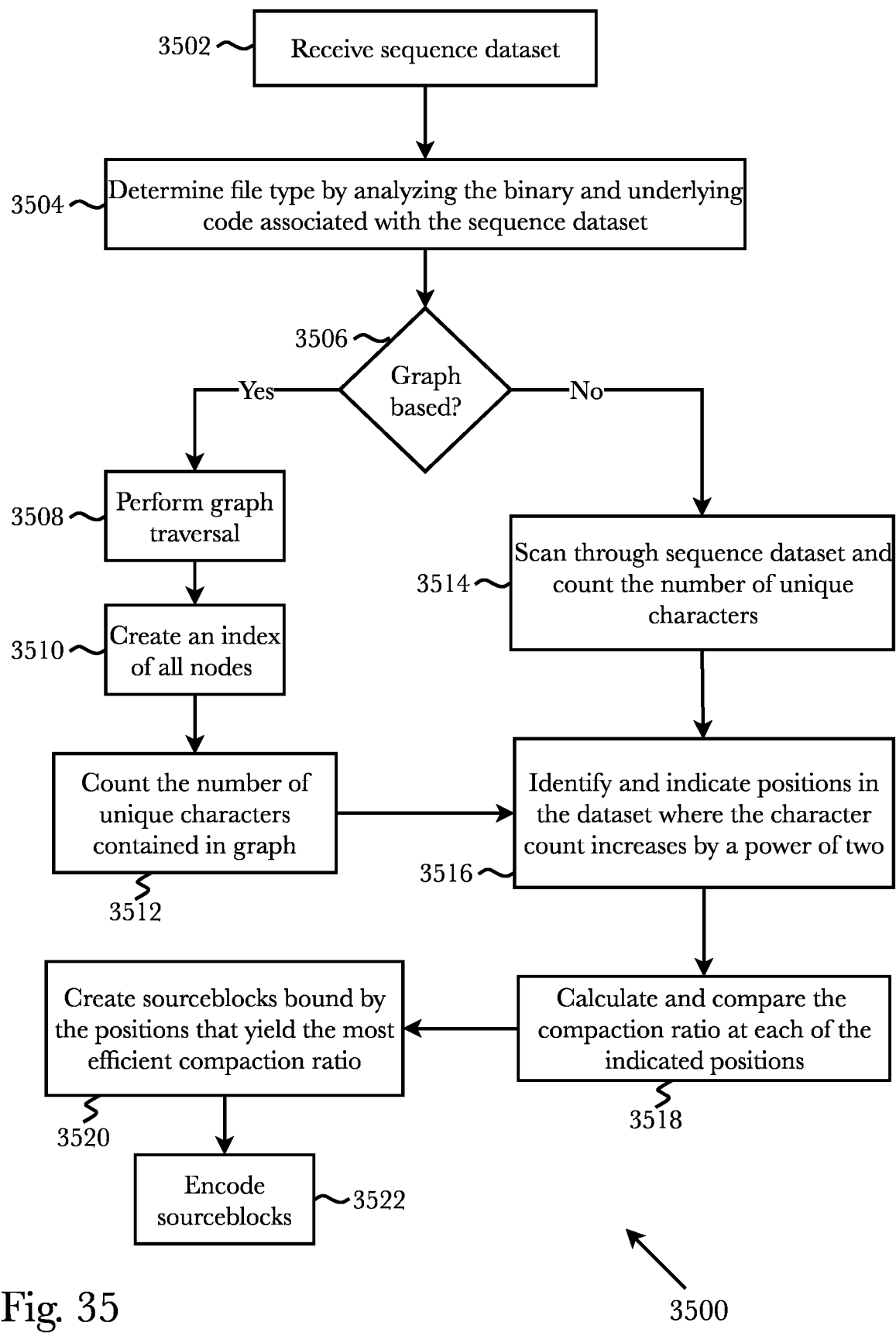
FIG. 35 is a method diagram of an exemplary method for scanning a sequence dataset, according to some embodiments.

FIG. 35 is a flow diagram of an exemplary method 3500 for scanning a sequence dataset, according to some embodiments. According to some embodiments, the process begins when a sequence analyzer 3410 receives a sequence dataset 3502. The sequence dataset may comprise genomic and/or bioinformatic information, and may be received by sequence analyzer 3410 in various file format types. As a next step, a sequence analyzer 3410 may analyze the sequence dataset in order to determine what type of file format was received by analyzing the binary and underlying code associated with the sequence dataset 3504. In some aspects, a database of known file types may be present which can be leveraged to compare the received sequence dataset file format against the known file types in order to assist system 3400 in determining the file correct file type. At a next step, 3506 the file type is labeled either as graph-based (e.g., genome graph, directed graph, etc.) or text-based (e.g., word file, CSV, FASTA, etc.). If the received sequence dataset is a graphical representation of genome sequences, then a 3508 graph traversal algorithm is selected and graph traversal is performed on the graph data, wherein as the graph is traversed, sequence analyzer 3410 may determine the reference node (that is, the node which serves as the origin of the graph) and assign a first index value to the reference node and then all subsequent nodes also receive an index value based on their position relative to the reference node 3510. As each node on the graph is traversed and indexed, the sequence data expressed by each node is also scanned and a count is maintained of the number of unique characters contained in the graph 3512 and an indication is made at positions in the graphical dataset where the character count increase by a power of two 3516. These indicated positions may be used by sequence analyzer 3410 as locations where sourceblock boundaries may be established. At the next step, compaction calculator 3416 may calculate and compare the compaction ratios of using sourceblocks bounded at the indicated positions 3518. The next step 3520 deconstructs the received sequence dataset to create a plurality of sourceblocks bound by the positions that yield the most efficient compaction ratio. As a last step, 3522 the plurality of sourceblocks can be sent to data deconstruction engine 3420 where they may be encoded using reference codes.

If, at step 3506, the file type is text-based, then sequence analyzer 3410 may scan through the sequence dataset and maintain a count of the unique characters contained within the received dataset 3514. The text-based sequence dataset then proceeds through steps 3516-3522 as described above. It should be appreciated that this diagram is an exemplary flow diagram and does not limit the disclosed system and method in any way. In some embodiments, actions and steps of this method may be done sequentially as is illustrated in FIG. 35. In other embodiments, parallel processing may be leveraged in order to perform some of the steps illustrated in parallel. For example, during graph traversal processes node indexing and counting unique characters can be performed in parallel with no loss of performance.

Figure 36A:
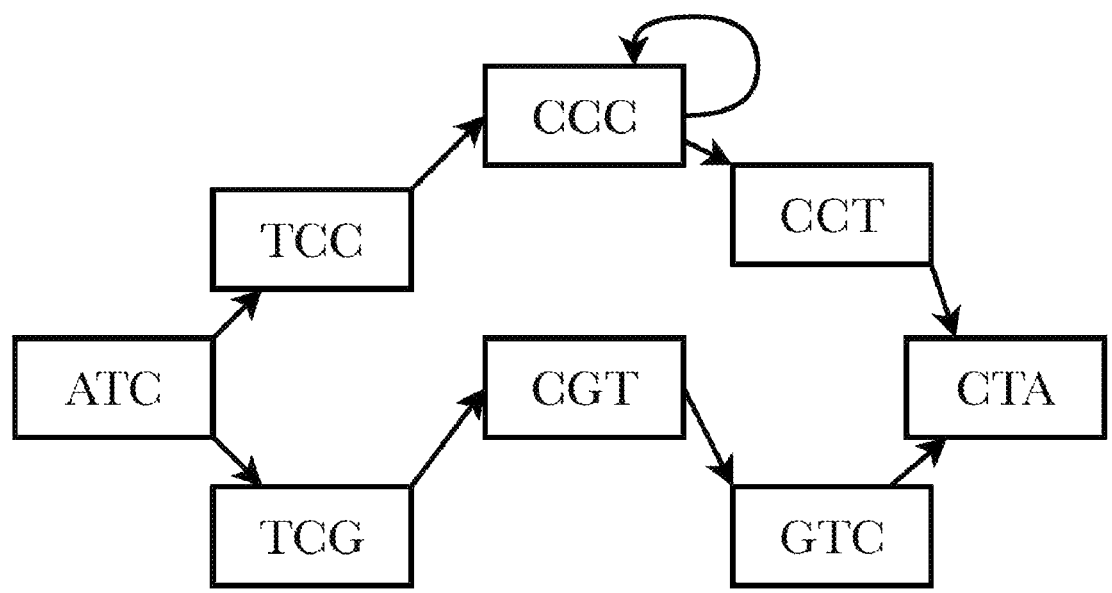

FIGS. 36A-D are exemplary genome graphs that may be processed by system 3400 for bandwidth-efficient encoding of genomic data, according to some embodiments. FIGS. 36A-D illustrate four different types of genome graphs, all constructed from the pair of sequences ATCCCCTA and ATGTCTA. Graphs have a longstanding place in biological sequence analysis, in which they have often been used to compactly represent an ensemble of possible sequences. FIG. 36A is a representation of a De Bruijin graph which is a directed graph representing overlaps between sequences of symbols, in this example the symbols are the genetic "letters" of the DNA code, G, C, T, and A, which stand for the various different chemicals that make up the nucleotide bases of DNA. A De Bruijin graph is comprised of vertices (nodes), consisting of all possible length-n sequences of the given symbols; the same symbol may appear multiple times in a sequence. If one of the vertices can be expresses as another vertex by shifting all its symbols by one place to the left and adding a new symbol at the end of the vertex, then the latter has a directed edge to the former vertex. Each vertex in a De Bruijin graph has the same number of input edges and output edges. De Bruijin graphs are popular directed graph representations in which each node represents a k-mer (a unique string of length k), and each directed edge represents an overlap of k−1 bases between the suffix of the "from" node and the prefix of the "to" node. De Bruijin graphs are a restricted class of vertex-labeled directed graphs. In bioinformatics, De Bruijin graphs are used for de novo assembly of sequencing reads into a genome.

Figure 36B:
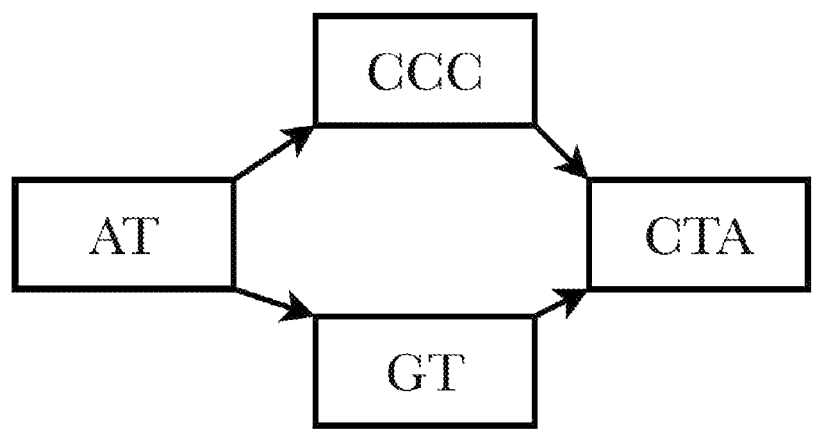

FIG. 36B is a representation of a directed acyclic graph (DAG) that is used to store and convey information about a genome sequence. DAGs may be the simplest common graph representation in which directed edges encode a nucleotide sequence. DAGs are graphs whose nodes are labeled such that a directed walk can be interpreted as a DNA sequence, defined by the sequence of node labels along the walk. In either edge- or vertex-labeled representations, directed graphs do not fully express the concept of strand. That is, they do not distinguish between reading a DNA molecule in its forward and reverse complement orientations.

Figure 36C:
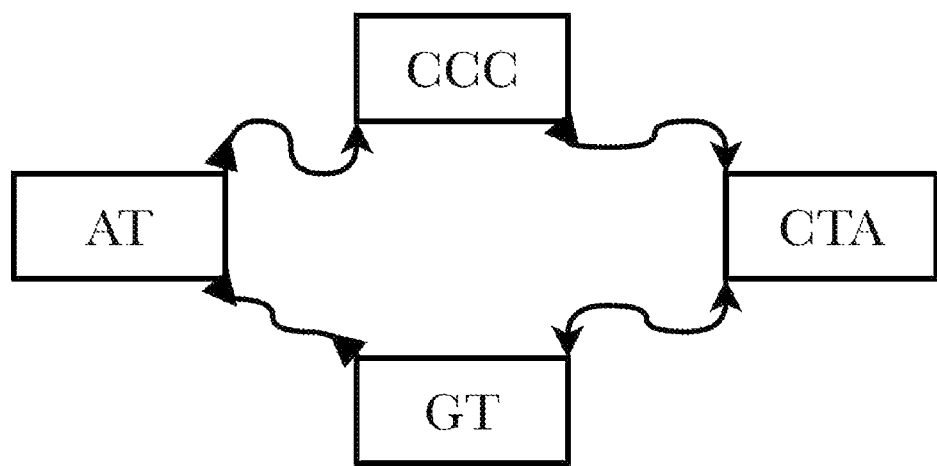

FIG. 36C is a representation of a bidirected graph (also referred to as a sequence graph). To express strandedness, directed graphs can be generalized to bidirected graphs in which each edge endpoint has an independent orientation, indicating whether the forward or reverse complement strand of the attached node is to be visited when entering the node through that endpoint of the edge. Inversions, reverse tandem duplications, and arbitrarily complex arrangements are expressible in the bidirected representation. Such complex variation cannot be expressed in the directed graph representation without creating independent forward and reverse complement nodes and storing additional information to describe information to describe this complementarity. Generally, a bidirected graph in which each node is labeled with a nucleotide string is referred to as a sequence graph. In a sequence graph, a DNA sequence is read out by concatenating the node-oriented labels of a walk that always enters and exits each node through edge endpoints with the opposite orientations. Labels are oriented such that entering through one endpoint orientation encodes the reverse complement of entering the node through the opposite endpoint orientation.

Figure 36D:
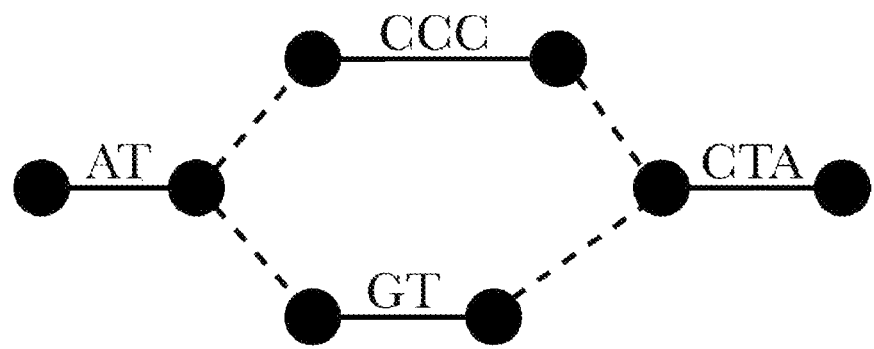

FIG. 36D is a representation of a bi-edged graph (also referred to as a bi-edged sequence graph). Bi-edged graphs are the edge-labeled version of bidirected graphs which give an equivalent representation.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 28:
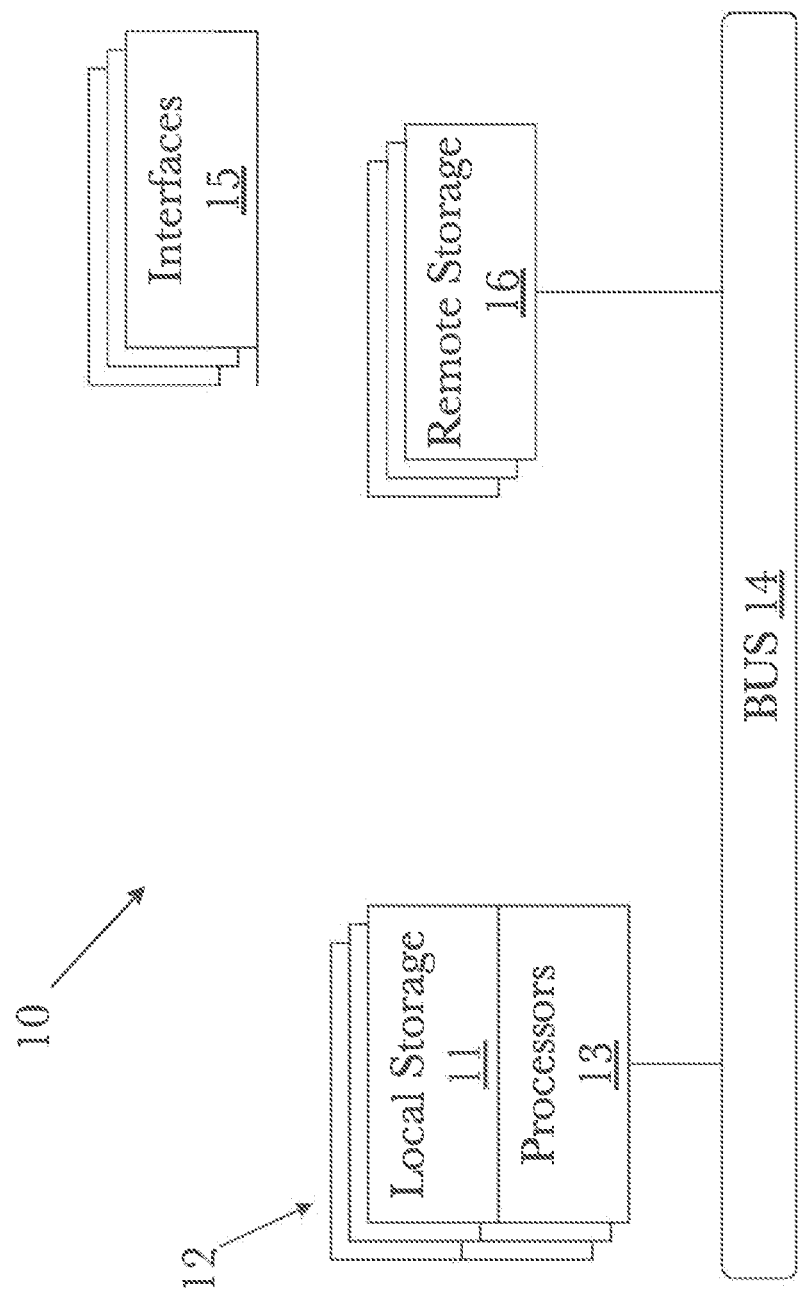
FIG. 28 is a block diagram illustrating an exemplary hardware architecture of a computing device.

Referring now to FIG. 28, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (Wi-Fi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 28 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 29:
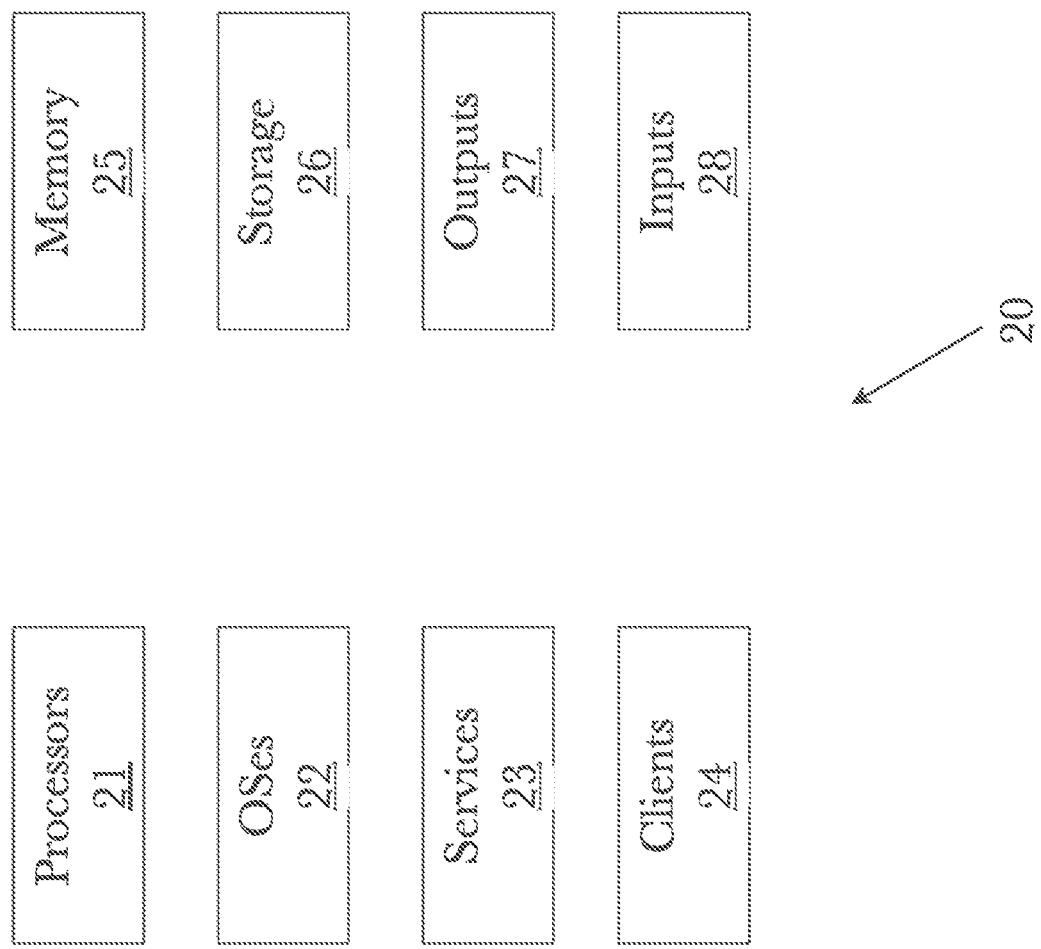
FIG. 29 is a block diagram illustrating an exemplary logical architecture for a client device.

In some aspects, systems may be implemented on a standalone computing system. Referring now to FIG. 29, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 28). Examples of storage devices 26 include flash memory, magnetic hard drive, CD-ROM, and/or the like.

Figure 30:
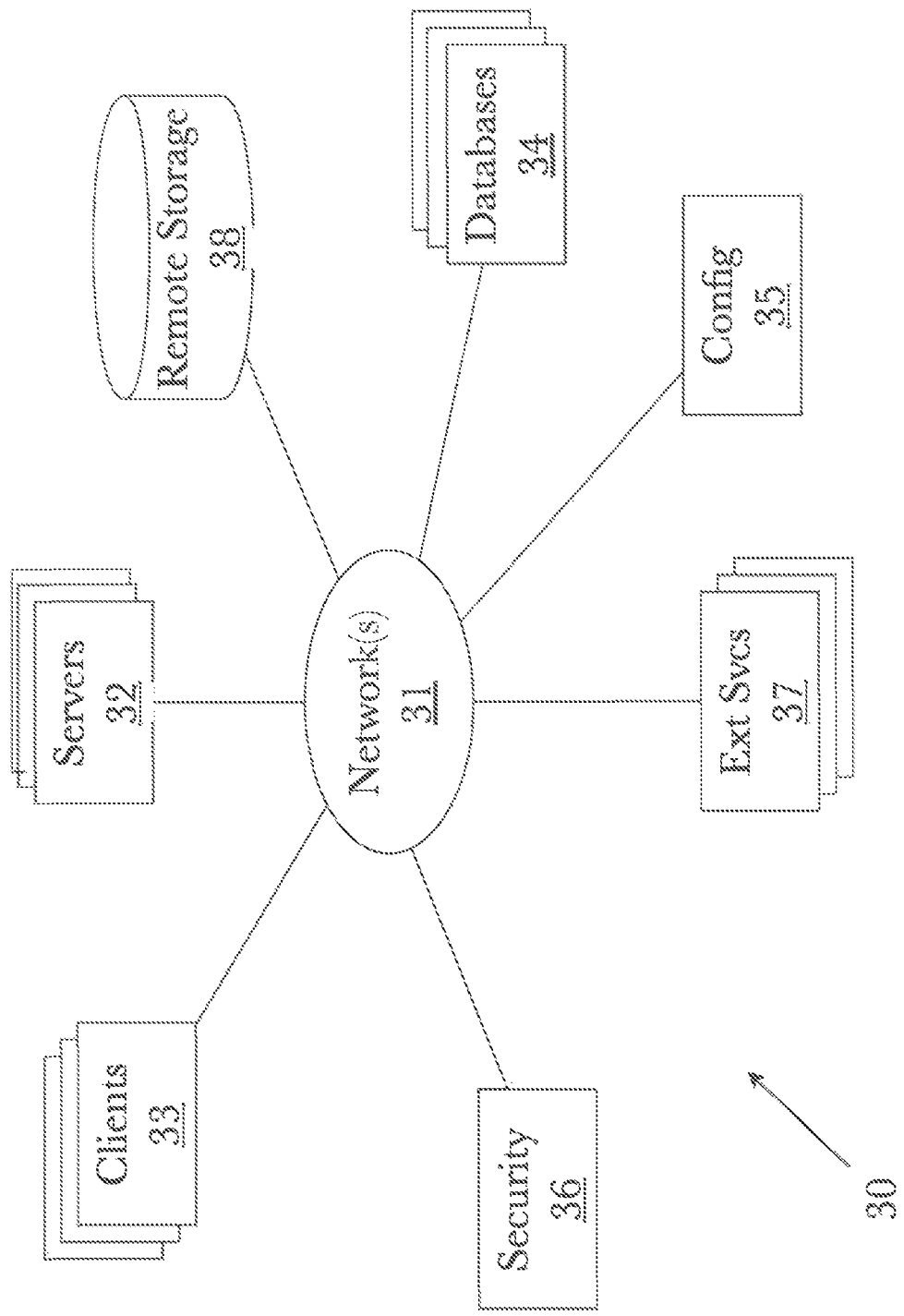
FIG. 30 is a block diagram showing an exemplary architectural arrangement of clients, servers, and external services.

In some aspects, systems may be implemented on a distributed computing network, such as one having any number of clients and/or servers. Referring now to FIG. 30, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 29. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as Wi-Fi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some aspects, clients 33 or servers 32 (or both) may make use of one or more specialized services or appliances that may be deployed locally or remotely across one or more networks 31. For example, one or more databases 34 may be used or referred to by one or more aspects. It should be understood by one having ordinary skill in the art that databases 34 may be arranged in a wide variety of architectures and using a wide variety of data access and manipulation means. For example, in various aspects one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 31:
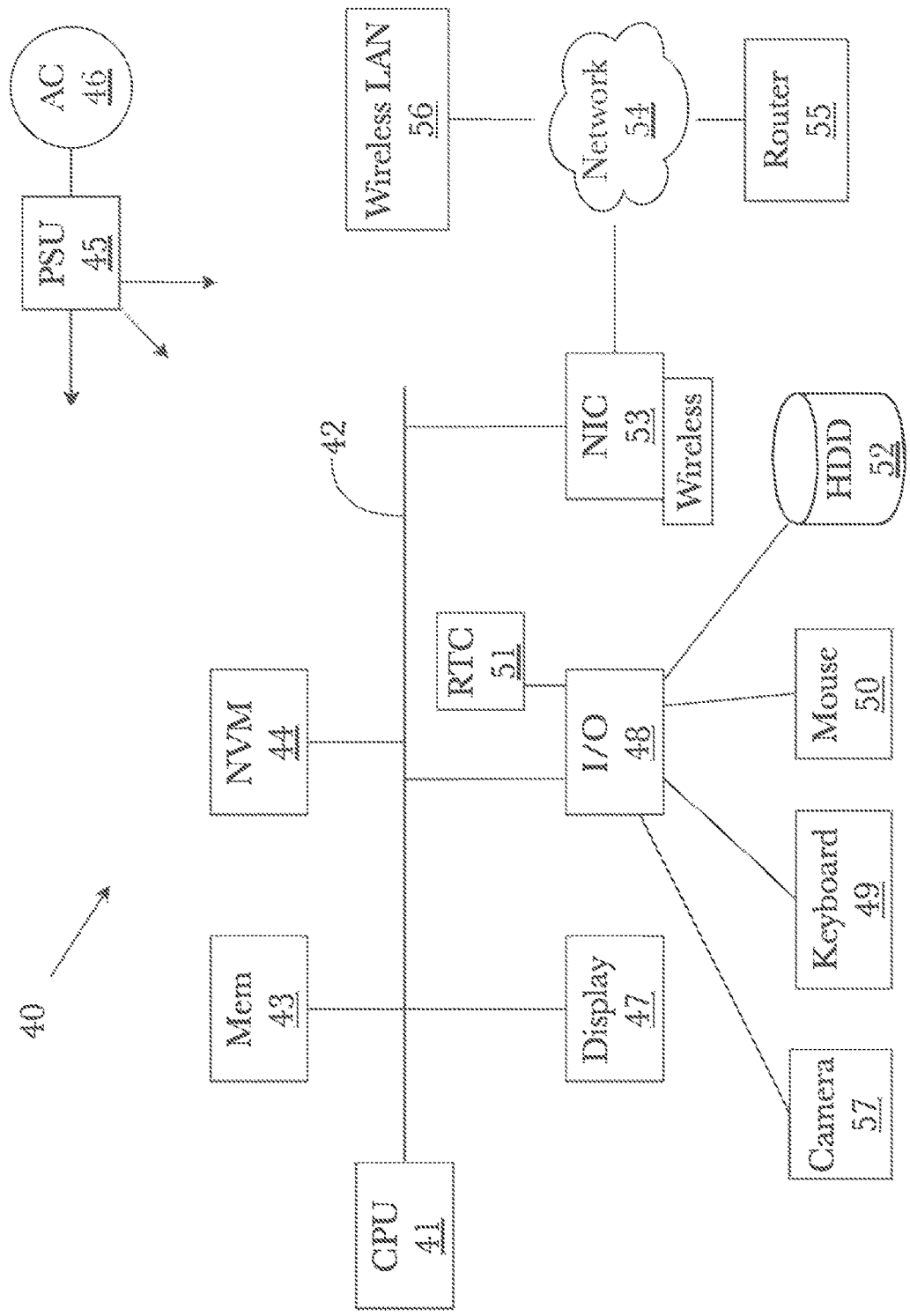
FIG. 31 is another block diagram illustrating an exemplary hardware architecture of a computing device.

FIG. 31 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for bandwidth-efficient encoding of genomic data, comprising:
   a computing device comprising a processor, and a memory;
   a codebook stored in the memory of the computing device, the codebook comprising a plurality of sourceblocks and, for each sourceblock, a reference code;
   a sequence analyzer comprising a first plurality of programming instructions stored in the memory and operable on the processor, wherein the first plurality of programming instructions, when operating on the processor, cause the processor to:
   receive a sequence dataset;
   scan the sequence dataset and maintain a count of the number of unique characters contained within the sequence dataset;
   for each occurrence of a unique character which causes the count of the number of unique characters to reach a value equal to a power of two:
   indicate a position in the sequence dataset corresponding to the unique character;
   calculate a compaction ratio that would be obtained by dividing the sequence dataset into one of a plurality of segments at one of the indicated positions;

deconstruct the sequence dataset into a plurality of deconstructed sourceblocks at the positions that yield the best compaction ratio; and pass the plurality of deconstructed sourceblocks to a data deconstruction engine; and a data deconstruction engine comprising a second plurality of programming instructions stored in the memory and operable on the processor, wherein the second plurality of programming instructions, when operating on the processor, cause the processor to:

receive the plurality of deconstructed sourceblocks from the sequence analyzer;

pass the plurality of deconstructed sourceblocks to a library management module for comparison with sourceblocks already contained in the codebook;

receive a reference code for each of the deconstructed sourceblocks from the library management module; and create a plurality of codewords for storage or transmission of the sequence dataset; and a library management module comprising a third plurality of programming instructions stored in the memory and operable on the processor, wherein the third plurality of programming instructions, when operating on the processor, cause the processor to:

receive the plurality of deconstructed sourceblocks from the data deconstruction engine;

for each of the plurality of deconstructed sourceblocks, return a reference code to the data deconstruction engine, when the respective received deconstructed sourceblock matches an existing sourceblock in the codebook; and for each received deconstructed sourceblock that is not present in the codebook:

create a new, unique reference code for the respective deconstructed sourceblock;

store both the respective deconstructed sourceblock and the associated reference code in the codebook; and return the new reference code to the data deconstruction engine.

2. The system of claim 1, wherein each of the plurality of codewords contains at least a reference code to a sourceblock in the codebook, and may contain additional information about the location of the reference code within the sequence dataset.

3. The system of claim 1, wherein the sequence dataset that is encoded comprises a graph representing at least a portion of a plurality of genomes.

4. The system of claim 3, wherein the graph is a De Bruijin graph, a directed graph, a bi-edged graph, or a bidirected graph.

5. The system of claim 1, further comprising a data reconstruction engine comprising a fourth plurality of programming instructions stored in the memory and operable on the processor, wherein the fourth plurality of programming instructions, when operating on the processor, cause the processor to:

receive a request for a reconstructed sequence dataset;

retrieve the codewords associated with the requested data from the codebook;

pass the reference codes contained in the codewords to the library management module for retrieval of the sourceblock contained in the codebook associated with the reference codes;

assemble the retrieved sourceblocks in proper order based on location information contained in the codewords; and send out the reconstructed sequence dataset to the requester.

6. A method for bandwidth-efficient encoding of genomic data, comprising the steps of:

storing, in a memory of a computing device, a codebook, the codebook comprising a plurality of sourceblocks and for each sourceblock a reference code;

receiving a sequence dataset;

scanning the sequence dataset and maintaining a count of the number of unique characters contained within the sequence dataset;

for each occurrence of a unique character which causes the count of the number of unique characters to reach a value equal to a power of two:

indicating a position in the sequence dataset corresponding to the unique character;

calculating a compaction ratio that would be obtained by dividing the sequence dataset into one of a plurality of segments at one of the indicated positions;

deconstructing the sequence dataset into a plurality of deconstructed sourceblocks at the positions that yield the best compaction ratio;

passing the plurality of deconstructed sourceblocks to a data deconstruction engine;

receiving the plurality of deconstructed sourceblocks from the sequence analyzer;

passing the plurality of deconstructed sourceblocks to a library management module for comparison with sourceblocks already contained in the codebook;

receiving a reference code for each of the deconstructed sourceblocks from the library management;

creating a plurality of codewords for storage or transmission of the sequence dataset;

receiving the plurality of deconstructed sourceblocks from the data deconstruction engine;

for each of the plurality of deconstructed sourceblocks, returning a reference code to the data deconstruction engine, when the respective received deconstructed sourceblock matches an existing sourceblock in the codebook; and for each received deconstructed sourceblock that is not present in the codebook:

creating a new, unique reference code for the respective deconstructed sourceblock;

storing both the respective deconstructed sourceblock and the associated reference code in the codebook; and returning the new reference code to the data deconstruction engine.

7. The method of claim 6, wherein each of the plurality of codewords contains at least a reference code to a sourceblock in the codebook, and may contain additional information about the location of the reference code within the sequence dataset.

8. The method of claim 6, wherein the sequence dataset that is encoded comprises a graph representing at least a portion of a plurality of genomes.

9. The method of claim 8, wherein the graph is a De Bruijin graph, a directed graph, a bi-edged graph, or a bidirected graph.

10. The method of claim 6, further comprising the steps of:
  receiving a request for a reconstructed sequence dataset;
  retrieving the codewords associated with the requested data from the codebook;
  passing the reference codes contained in the codewords to the library management module for retrieval of the sourceblock contained in the codebook associated with the reference codes;
  assembling the sourceblock in the proper order based on the location information contained in the codewords; and
  sending out the reconstructed sequence dataset to the requester.

* * * * *